(12) United States Patent
Wang et al.

(10) Patent No.: US 9,597,290 B2
(45) Date of Patent: Mar. 21, 2017

(54) PARTICLE FUNCTIONALIZATION

(71) Applicant: Regents of the University of Minnesota, Minneapolis, MN (US)

(72) Inventors: Jian-Ping Wang, Shoreview, MN (US); Claire Hovland, Andover, MN (US); Timothy Bloomquist, Shoreview, MN (US); Jing Ying, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 14/826,684

(22) Filed: Aug. 14, 2015

(65) Prior Publication Data

US 2015/0352210 A1    Dec. 10, 2015

Related U.S. Application Data

(63) Continuation of application No. PCT/US2014/016473, filed on Feb. 14, 2014.

(60) Provisional application No. 61/765,444, filed on Feb. 15, 2013.

(51) Int. Cl.
| | | |
|---|---|---|
| *A61K 9/14* | (2006.01) | |
| *A61K 47/02* | (2006.01) | |
| *B22F 9/12* | (2006.01) | |
| *C23C 14/35* | (2006.01) | |
| *H01J 37/34* | (2006.01) | |
| *B22F 9/04* | (2006.01) | |
| *B01J 2/02* | (2006.01) | |
| *B22F 1/00* | (2006.01) | |
| *B01J 2/04* | (2006.01) | |

(52) U.S. Cl.
CPC ............ *A61K 9/14* (2013.01); *A61K 47/02* (2013.01); *B01J 2/02* (2013.01); *B01J 2/04* (2013.01); *B22F 1/0062* (2013.01); *B22F 9/04* (2013.01); *B22F 9/12* (2013.01); *C23C 14/35* (2013.01); *H01J 37/34* (2013.01); *B22F 2202/05* (2013.01); *B22F 2998/10* (2013.01); *B22F 2999/00* (2013.01); *C22C 2202/02* (2013.01)

(58) Field of Classification Search
None
See application file for complete search history.

(56) References Cited

U.S. PATENT DOCUMENTS

| | | | |
|---|---|---|---|
| 3,669,860 A | 6/1972 | Knowles et al. | |
| 4,938,949 A | 7/1990 | Borch et al. | |
| 5,178,739 A | 1/1993 | Barnes et al. | |
| 5,228,963 A | 7/1993 | Rose | |
| 5,334,302 A | 8/1994 | Kubo et al. | |
| 5,482,611 A | 1/1996 | Helmer et al. | |
| 5,897,945 A | 4/1999 | Lieber et al. | |
| 6,077,403 A | 6/2000 | Kobayashi et al. | |
| 6,077,406 A | 6/2000 | Kawakubo et al. | |
| 6,337,001 B1 | 1/2002 | Haag et al. | |
| 6,899,054 B1 | 5/2005 | Bárdos et al. | |
| 7,332,351 B2 | 2/2008 | Tan et al. | |
| 9,242,003 B2 | 1/2016 | Ayoub et al. | |
| 2006/0081467 A1 | 4/2006 | Nagashima et al. | |
| 2007/0089983 A1 | 4/2007 | Plaisted et al. | |
| 2007/0175749 A1 | 8/2007 | Schneider et al. | |
| 2009/0020416 A1 | 1/2009 | Scholhammer et al. | |
| 2009/0255802 A1 | 10/2009 | Donchev et al. | |
| 2009/0297615 A1 | 12/2009 | Wang | |
| 2010/0126848 A1 | 5/2010 | Ohmi et al. | |
| 2012/0027865 A1 | 2/2012 | Sahoo et al. | |
| 2012/0181171 A1 | 7/2012 | Wang et al. | |
| 2013/0195752 A1 | 8/2013 | Panyam et al. | |
| 2013/0243699 A1 | 9/2013 | Wang et al. | |
| 2015/0376772 A1 | 12/2015 | Wang et al. | |

FOREIGN PATENT DOCUMENTS

| | | |
|---|---|---|
| CA | 2326202 A1 | 10/1999 |
| CN | 101297059 | 10/2008 |
| CN | 201545907 | 8/2010 |
| EP | 2136388 | 12/2009 |

(Continued)

OTHER PUBLICATIONS

Shen et al. Monocrystalline iron oxide nanocompounds (MION): physicochemical properties. 1993 Magn. Reson. 604. Med. 29: 599-604.*
Lu et al., "Magnetic nanoparticles: synthesis, protection, functionalization, and application," Angew Chem Int Ed Engl., 46(8)1222-1244, Feb. 12, 2007.
Wu et al., "Interaction of fatty acid monolayers with cobalt nanoparticles," Nano Letters 4(2): 383-386, Feb. 2004 .
"Tiniest magnets shape up," Nature, 447: 888, Jun. 2007.
Amekura et al., "Curie transition of superparamagnetic nickel nanoparticles in silica glass: A phase transition in a finite size system," Phys. Rev. B, 71, 172404 (2005).
Bai et al., "(FeCo)3Si—SiOx core—shell nanoparticles fabricated in the gas phase," Nanotechnology, 18(6):065701, 5 pages, 2007.
Bai et al., "Cubic and Spherical High-Moment FeCo Nanoparticles With Narrow Size Distribution" IEEE Transactions on Magnetics, 43(7):3340-3342, Jul. 2007.

(Continued)

Primary Examiner — Michael G Hartley
Assistant Examiner — Jennifer Lamberski
(74) Attorney, Agent, or Firm — Fish & Richardson P.C.

(57) ABSTRACT

Particle functionalization systems including one or more of: a target of a material; an energetic ion and/or electron source providing accelerated ions and electrons to the target; a potential that is applied to at least the target and that causes ions and/or electrons from the ionized gas to impact a surface of the target and release atoms of the material; at least one magnet providing a magnetic field that controls movement of the ions and electrons and nucleation, formation and growth of particles from the released atoms; and a particle collection device that collects particles, the collection device comprising a substrate and a polymeric functionalization coating disposed on the substrate, wherein particles impinge upon and form bonds with molecules of the functionalization coating. Methods of preparing functionalized particles, functionalized particle compositions, and kits including functionalized particles are also described.

17 Claims, 9 Drawing Sheets

(56) References Cited

FOREIGN PATENT DOCUMENTS

| EP | 2136388 A1 | 12/2009 |
|---|---|---|
| RU | 2224050 | 2/2004 |
| RU | 2361013 | 7/2009 |
| RU | 2385967 | 11/2009 |
| WO | WO2005025508 | 3/2005 |
| WO | WO 2009149563 | 12/2009 |
| WO | WO 2011020294 | 2/2011 |
| WO | WO 2012097268 | 7/2012 |
| WO | WO 2014121122 | 8/2014 |

OTHER PUBLICATIONS

Belayachi et al., "Critical analysis of magnetically semi-disordered systems: critical exponents at various transitions," *Journal of Physics: Condensed Matter*, 10(7):1599, 1998.
Brezovich et al., "Temperature distributions in tumor models heated by self-regulating nickel-copper alloy thermoseeds," *Medical physics*, 11(2):145-152, 1984.
Brusentsova et al., "Synthesis and investigation of magnetic properties of Gd-substituted Mn—Zn ferrite nanoparticles as a potential low-T C agent for magnetic fluid hyperthermia," *Journal of Magnetism and Magnetic Materials*, 293(1): 298-302, 2005.
Chanéac et al., "Magnetic iron oxide—silica nanocomposites. Synthesis and characterization," *Journal of Materials Chemistry*, 6(12):1905-1911, 1996.
Chen et al., "MnBi films for magnetooptic recording," *Magnetics, IEEE Transactions on* ,9(2):66-83, Jun. 1973.
Glaspell et al., "A room-temperature and microwave synthesis of M-doped ZnO (M=Co, Cr, Fe, Mn & Ni)," *Journal of cluster science*, 16(4):523-536, 2005.
Hergt et al., "Magnetic particle hyperthermia: nanoparticle magnetism and materials development for cancer therapy," *J. Phys. Condens. Matter* 18(38): S2919-S2934, 2006.
Herzer, "Grain structure and magnetism of nanocrystalline ferromagnets," *IEEE Trans. Magn.*, 25(5):3327-3329, 1989.
Jing et al., "Fabrication of heuslar Fe3Si nanoparticles," *J. Appl. Phys.*, 105, 07B520:1-07B520:3, 2009.
Jung et al., "Gas flow sputtering of oxide coatings: practical aspects of the process," *Surface and Coatings Technology*, 86-87 (Part 1):218-224, Apr. 22, 1996, Dec. 1, 1996.
Keblinski et al., "Limits of localized heating by electromagnetically excited nanoparticles," *Journal of Applied Physics*, 100(5), 054305, 2006.
Kim et al. "Magnetic fluorescent delivery vehicle using uniform mesoporous silica spheres embedded with monodisperse magnetic and semiconductor nanocrystals." *Journal of the American Chemical Society* 128(3):688-689, 2006.
Li et al., "Direct synthesis of highly ordered Fe-SBA-15 mesoporous materials under weak acidic conditions," *Microporous and mesoporous materials*, 84(1): 41-49, 2005.
Li et al., "Growth and control of microscale to nanoscale carbon nitride particles," *Appl Phys Lett.*, 89(14):142901-1-142901-3, Oct. 2, 2006
Maier-Hauff et al., "Intracranial thermotherapy using magnetic nanoparticles combined with external beam radiotherapy: results of a feasibility study on patients with glioblastoma combined with external multiforme," *Journal of neuro-oncology*, 8(1):53-60, 2007.
Martelli et al., "Synthesis of Fe—Si nanoparticles by cw CO 2 laser assisted pyrolysis from gaseous precursors," *Applied surface science* 186(1): 562-567, 2002.
McCallum, "Determination of the saturation magnetization, anisotropy field, mean field interaction, and switching field distribution for nanocrystalline hard magnets," *J. Magn. and Magn. Mater.*, 292:135-142, Apr. 2005.
McNemy et al., "Chemical synthesis of monodisperse -Fe—Ni magnetic nanoparticles with tunable Curie temperatures for self-regulated hyperthermia," *J. App. Phys.*, 107, 09A312, 2010.
Neuber and Heilmann, "Laser welding of transparent high performance polymer foils by using silver nanoparticles as absorption layer," *Mater. Res. Symp. Proc.*, vol. 1365: 81-86, Jan. 1, 2011.
Ohnuma et al., "Magnetic properties of amorphous FeCo base ultrafine particles," *IEEE Transactions on Magnetics*, vol. Mag-22, No. 5, pp. 1098-1100, Jan. 1, 1986, Sep. 1986.
Pankhurst et al., "Applications of magnetic nanoparticles in biomedicine," *Journal of physics* D: Applied physics, 36(13): R167, 2003.
Pollert et al., "New TcTc-tuned magnetic nanoparticles for self-controlled hyperthermia," *J. Magn. and Magn. Mater.*, 316(2): 122-125, Sep. 2007.
Qiu and Wang, "Monodispersed and highly ordered L10 FePt nanoparticles prepared in the gas phase," *Applied Physics Letters*, 88(19):192505-3, Epub May 2006.
Qui and Wang, "Tuning the Crystal Structure and Magnetic Properties of FePt Nanomagnets," *Adv. Mater.* 19(13):1703-1706, Jun. 2007.
Sohn and Victora, "Optimization of magnetic anisotropy and applied fields for hyperthermia applications," *J. Appl. Phys.*, 107(09B312), 2010.
Staunton et al., "Temperature dependence of magnetic anisotropy: An ab initio approach," *Physical Review B*, 74(14): 144411, 2006.
Taylor et al., "Magnetic nanoparticles and a magnetic field for the rapid removal of device related infections." In Bioengineering Conference (NEBEC), 2011 *IEEE 37th Annual Northeast*, pp. 1-2. IEEE, 2011.
Tie et al., "Phases in ball-milled. *Journal of Physics: Condensed Matter*," 9(6): 1381, 1997.
Varadwaj et al., "Phase-controlled growth of metastable Fe5Si3 nanowires by a vapor transport method," *Journal of the American Chemical Society*, 129(27): 8594-8599, 2007.
Veintemillas-Verdaguer et al., "Continuous production of inorganic magnetic nanocomposites for biomedical applications by laser pyrolysis," *Journal of Magnetism and Magnetic Materials*, 311(1):120-124, 2007.
Xu and Wang, "Direct gas-phase synthesis of hetero structured nanoparticles through phase separation and surface segregation," *Adv. Mater.*, 20(5): 994-999, 2008.
Xu and Wang, "FeCo—Au core-shell nanocrystals," *Applied Physics Letters*, 91(23):233107-3, Dec. 2007.
Zhang et al., "Carbon nanotube template-assisted synthesis of zinc ferrite nanochains," *Chemistry and Physics.*, 124(2): 1029-1033, 2010.
Zhang et al., "Electronic structure and magnetism of Fe-doped SiC nanotubes", *Science China*, 53(9): 1582-1589, Sep. 2010.
European Search Report for EP App. No. 12734741.7 dated Jul. 22, 2014, 8 pages.
International Preliminary Report on Patentability for PCT/US2012/021269 issued Jul. 16, 2013, 5 pages.
International Search Report and Written Opinion for PCT/US2012/021269, mailed Aug 22, 2012, 9 pages.
International Preliminary Report on Patentability for PCT/US2014/014264, mailed Aug. 13, 2015, 6 pages.
International Search Report and Written Opinion for PCTUS2014014264, mailed Mar. 31, 2014, 9 pages.
International Preliminary Report on Patentability for PCT/US2014/016473, mailed Aug. 27, 2015, 9 pages.
International Search Report and Written Opinion for PCTUS2014016473, mailed Jul. 16, 2014, 12 pages.
U.S. Appl. No. 13/350,421, filed Jan. 13, 2012, Jian-Ping et al.
U.S. Appl. No. 13/708,658, filed Dec. 7, 2012, Jian-Ping et al.
U.S. Appl. No. 14/765,284, filed Jul. 31, 2015, Jian-Ping et al.
Kraynev, "Mechanics," Fundamental Dictionary, Mashinostroenye, p. 661, col. 1, 2000.
Polyak, "Hardening technology," "Mashinostroenye" "L.B.M.— Script" vol. 1, p. 314, paragraph 3, pp. 311, 31, 1995.

\* cited by examiner

PARTICLE FUNCTIONALIZATION

CROSS-REFERENCE TO RELATED APPLICATION

This application is a continuation of International Application No. PCT/US2014/016473, filed Feb. 14, 2014, which claims benefit of U.S. Provisional Application No. 61/765,444, filed Feb. 15, 2013, all of which are incorporated herein by reference in their entirety.

TECHNICAL FIELD

This document relates to particles.

BACKGROUND

Particles have many applications in industry, research and medicine, among others. A particle can be ascribed several physical or chemical properties (such as volume or mass). As the size of a particle decreases, these properties change as compared to the bulk metal. The size, and hence the surface area of a particle, can impact the physical, chemical and/or pharmacologic properties of the material forming the particle.

Within this broad arena, particles with a size in the micro or nano scale are useful in a wide variety of applications. Nanoparticles are generally understood to encompass microscopic particles with at least one dimension less than 100 nm, while microparticles are generally understood to encompass particles in the range of 0.1 to 100 µm in size. In a further area, nanoparticles fabricated of magnetic materials have attracted increasing interest among researchers of various fields due to their promising applications in such diverse areas as biomedicine, magnetic resonance imaging (MRI), cell and DNA separation, drug delivery, gene cloning, hyperthermia for cancer therapy, and magnetic recording media.

Naked metallic particles are chemically highly active, and are easily oxidized in air, which can result in loss of magnetism and/or dispersibility. Particles with small size, e.g., less than 10 nm, have more active surfaces and could easily interact with any matrix materials (e.g., $H_2O$ and/or chemicals around them during their preparation stage). Therefore, maintaining the stability of metal particles for an extended period without agglomeration or precipitation is an important issue. Stability is a crucial requirement for almost any application of metallic particles. Especially pure metals, such as Fe, Co, Ni, Mn, Ti, Cr, Ca Al, Ag and Zn and their metal alloys, are very sensitive to air. Thus, a significant difficulty for use of pure metals or alloys arises from their instability towards oxidation in air; moreover, the susceptibility towards oxidation becomes higher the smaller the particles are. Particles in the micro- and nano-scale range exhibit intrinsic instability over longer periods of time. Such small particles tend to form agglomerates to reduce the energy associated with the high surface area to volume ratio of the micro- or nano-sized particles.

SUMMARY

Particle functionalization systems, methods for preparing functionalized particles, compositions comprising such particles, kits including the particles, and uses thereof are described herein. Particles include metal particles. In some implementations, the metal particles are magnetic particles. Novel functionalized metal particles in accordance with inventive principles can exhibit improved properties as compared to other metal particle preparations. In particular, inventive concepts provide novel particles comprising a metallic core having a surface functionalized with one or more polymers in a manner that provides improved or enhanced capabilities to the overall particle. Metal particles prepared in accordance with inventive concepts may be used in a wide variety of medical, industrial and research applications.

In some aspects, particles can be functionalized as they are generated, which can eliminate undesirable reactions at the surface of the particles. For example, when particles are generated in a vacuum or an ultra high vacuum (UHV) environment, surface functionalization can be provided within that vacuum environment and before the particles are exposed to environmental conditions outside the vacuum. Potential oxidation in air can be minimized or avoided. Inventive methods can thus provide streamlined, one-step functionalization processes for particles.

Implementations can provide any or all of the following advantages. Creation of metal particles can be improved. Particles can be functionalized as they are created. Particles of heterogeneous structure can be generated more efficiently. Functionalized surfaces in accordance with inventive concepts can change or improve the properties of the particle surface. In some implementations, inventive functionalized surfaces can provide a coated layer that is useful for the immobilization of other agents, for example, chemical moieties or biological agents such as small molecules, proteins, nucleic acids or cells. Functionalized particles in accordance with inventive principles can provide advantages such as high dispersion, high reactivity and easy separation.

In a first aspect, a particle functionalization system includes: a target of a material; a gas source providing sputtering gas to the target; a potential that is applied to at least the target and that causes ions from the ionized gas to impact a surface of the target and release atoms of the material; at least one magnet providing a magnetic field that controls movement of the ions and electrons and nucleation, formation and growth of particles from the released atoms; and a particle collection device that collects the as-prepared particles, the collection device comprising a substrate and a polymeric functionalization coating disposed on the substrate, wherein particles impinge upon the coating and form bonds with molecules of the functionalization coating.

Implementations can include any or all of the following features. The particles can be metal particles. The particles can be composed of FeCo, FeCo—FeCoO, FeCo—Au, FeCo—Ag, FeCo—$SiO_2$, FeCo—$TiO_2$, Fe—Ag, Co—Au, C, and Fe—Au, Fe—$TiO_2$, $Fe_5Si_3$, $Fe_3Si$, $Fe_{16}N_2$, FeN, $FeSi_3$—Au, $Fe_5Si_3$—$SiO_2$, $Fe_5Si_3$—Au, $Fe_{16}N_2$—Fe(N), $Fe_{16}C_2$, $Fe_{16}C_2$—Au, $Fe_{16}N_2$—Au, $Fe_{16}N_2$—Ag, $Fe_{16}N_2$—$Al_2O_3$, $Fe_{16}N_2$—$TiO_2$, or $Fe_{16}N_2$—$SiO_2$. The functionalization polymer can be selected from vinyl polymers, fatty acids, polyethers, polyesters, acrylic polymers, and aromatic polymers. In one embodiment, the functionalization polymer is a monofunctional polymer comprising a functional group selected from hydroxyl (—OH), carboxyl (—COOH), thiol (—SH), phosphate (—$PO_4^{3-}$), sulfate (—$SO_4^{2-}$), aldehyde (—CHO), and sulfide ($S^{2-}$). In another embodiment, the functionalization polymer comprises a bifunctional polymer comprising a first functional group and a second functional group. The second functional group can be the same or different from the first functional group. The second functional group is independently selected from hydroxyl (—OH), carboxyl (—COOH), thiol (—SH), phosphate (—PO$_4^{3-}$), sulfate (—SO$_4^{2-}$), aldehyde (—CHO) and sulfide (S$^{2-}$).

In another aspect, a method of preparing functionalized particles includes: introducing a sputtering gas (e.g., Ar, Ne, Kr and/or a mixture with He) into a particle source under ultra high vacuum conditions; ionizing the gas; passing the ionized gas through a plasma region in the opening(s) between targets or through the targets to liberate atoms from the target, thereby yielding a plasma comprising the liberated atoms; condensing the plasma comprising the liberated atoms to yield particles; collecting the particles on a collection device that comprises a substrate and a polymeric functionalization coating disposed on the substrate, wherein the particles impinge upon and form bonds with molecules of the functionalization coating.

Implementations can include any or all of the following features. The process can further comprise drying the deposited particles, thereby yielding functionalized metal particles in a dry form. In some implementations, the process can further comprise dissolving the support containing deposited particles in a suitable solvent, thereby dispersing the particles in water or an organic solvent. Suitable organic solvents can be selected based upon the material used to formulate the support. Illustrative organic solvents include, but are not limited to, chloroform, 2-butanone, methanol, ethanol, benzene, and the like. The support containing deposited particles can be washed, thereby liberating the functionalized particles from the collection device.

In further aspects, functionalized particles include: a metal core and a coating layer, the coating layer comprising at least one polymer, wherein the polymer is bound directly to the surface of the metal core.

In further aspects, functionalized particles include: multimetal cores (or a cluster of many metal cores) and a coating layer, the coating layer comprising at least one polymer, wherein the polymer is bound directly to the surface of the multi-metal cores.

Implementations can include any or all of the following features. The metal core can comprise a magnetic particle. In some aspects, the metal core comprises a superparamagnetic particle core. Illustrative materials for metal particles can comprise one or more of: iron, silicon, nitrogen, carbon, and/or cobalt. Examples of superparamagnetic particle materials include, but are not limited to, FeCo, FeCo—FeCoO, FeCo—Au, FeCo—Ag, FeCo—SiO$_2$, FeCo—TiO$_2$, Fe—Ag, Co—Au, C, and Fe—Au, Fe—TiO$_2$, Fe$_5$Si$_3$, Fe$_3$Si, Fe$_{16}$N$_2$, FeN, FeSi$_3$—Au, Fe$_5$Si$_3$—SiO$_2$, Fe$_5$Si$_3$—Au, Fe$_{16}$N$_2$—Fe(N), Fe$_{16}$C$_2$, Fe$_{16}$C$_2$—Au, Fe$_{16}$N$_2$—Au, Fe$_{16}$N$_2$—Ag, Fe$_{16}$N$_2$—Al$_2$O$_3$, Fe$_{16}$N$_2$—TiO$_2$, or Fe$_{16}$N$_2$—SiO$_2$.

The particle core can be provided with a coating of one or more polymers. In some aspects, the polymer comprises an inert and nontoxic polymer. Illustrative polymers include, but are not limited to, vinyl polymers, fatty acids, polyethers, polyesters, acrylic polymers, and aromatic polymers.

The polymer can include one or more functional groups to facilitate bonding to the particle core. In some aspects, a first functional group is a moiety that is capable of donating electrons to the particle to form a bond with a particle surface, thereby forming a bond between the polymer and the particle surface. For example, in some embodiments, the polymer can include a first functional group such as hydroxyl (—OH), carboxyl (—COOH), thiol (—SH), phosphate (—PO$_4^{3-}$), sulfate (—SO$_4^{2-}$), aldehyde (—CHO), sulfide (S$^{2-}$), or the like, which functional group is capable of binding metal particles.

Optionally, the polymer can include a second functional group capable of binding compounds to the particle. In accordance with these aspects, the functionalized particle can provide a customizable particle that can be tailored to a particular application by coupling a selected compound to the second functional group. The selection of the particular compound is thus left to an end user. Illustrative compounds that can bind to inventive particles can include, but are not limited to, small molecules, proteins, nucleic acids, targeting ligands, peptides, antibodies, antibody fragments, detectable moieties, bioactive agents (such as drugs), imaging agents, and the like.

In some embodiments, the functionalized particles are in a substantially dry form.

In additional embodiments, there is further provided an aqueous dispersion of the functionalized particles. The particles can be dispersed in water or in a buffer, as desired.

In still further embodiments, there is provided a kit comprising functionalized metal particles in a dry form, and or more additional components such as a solvent for dispersing the particles, additional compounds to be coupled to the functionalized particles, buffers, additional reagents, and the like. Optionally, the kit can comprise a dispersion of functionalized metal particles, the dispersion comprising an aqueous or organic solvent or buffer.

In further embodiments, there is provided a kit comprising functionalized particles and/or assemblies of particles in a dry form, and one or more additional components such as a solvent for dispersing the particles and/or additional compounds to be coupled to the functionalized particles. The size of particles and/or assemblies of particles could be ranged from 10 nm up to several hundred nanometers. The particles and/or clusters of particles could be non magnetic materials and/or mixture of magnetic materials and non magnetic materials. Optionally, the kit can comprise a dispersion of functionalized particles and/or assemblies of particles, the dispersion comprising an aqueous or organic solvent or buffer.

In some aspects, a pharmaceutical composition includes: a functionalized particle and a pharmaceutically acceptable carrier.

The details of one or more implementations are set forth in the accompanying drawings and the description below. Other features and advantages will be apparent from the description and drawings, and from the claims.

DESCRIPTION OF DRAWINGS

Like reference symbols in the various drawings indicate like elements.

DETAILED DESCRIPTION

Figure 1:
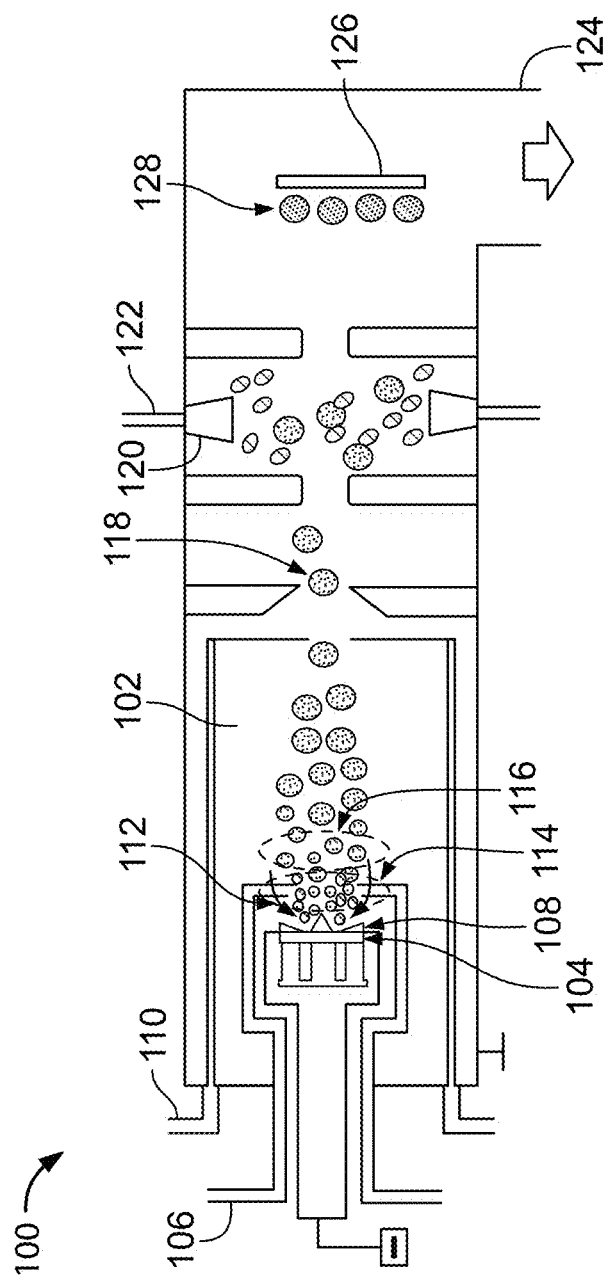
FIG. 1 shows an example of a system that can be used for spray functionalization of particles.

This document describes systems and techniques for functionalization of particles. The inventive systems and techniques are scalable for mass production and provide functionalized particles that can be used directly or can be further customized by users in a wide variety of applications. Thus, in some implementations, functionalized particles are contemplated that can provide enhanced or improved properties as compared to bare particles or particles coated with materials through other methods (such as emulsion or coupling methods performed outside vacuum conditions). In other implementations, the functionalized particles provide customizable tools that can provide a platform for an end user to couple additional desired compounds selected for particular applications.

In some implementations, particles can be functionalized as they are generated, which can eliminate adverse interaction between the particles and air. For example, as particles are traveling, a coating material can be sprayed to form a mist or aerosol, and the particles can react with the molecules of the coating material as they pass through. Alternatively, the coating material could be co-sputtered to coat the initially formed particles. For example, polymer or other chemicals can be evaporated to coat particles in-flight. As another example, a coating material can be deposited on a substrate, the substrate being located within the vacuum sputtering environment. In these aspects, particles can be caused to impinge on the substrate, thereby reacting with the molecules of the coating material.

Inventive methods and systems can be used to generate a wide variety of particles, in terms of size, material and shape. In some implementations, inventive methods and systems can be used to produce nanoparticles. The term "nanoparticle" is used herein to denote a microscopic particle smaller than about 100 nm in diameter, wherein each nanoparticle behaves as a complete unit in terms of the transport characteristics and physical and chemical properties. While nanoparticles are useful to illustrate many advantages of inventive concepts, it will be readily appreciated that inventive concepts are not limited to generation of nano-scale particles, but rather have application to a wide variety of particle sizes, as desired. Thus, discussion of nanoparticle embodiments is to be construed as illustrative only, and not limiting the scope of inventive concepts.

Inventive methods and systems can be particularly useful for producing metal particles, as these particles can be generated in a vacuum environment (for example, UHV). In some aspects, inventive methods and systems can be used to for magnetic particles. In still further embodiments, inventive methods and systems can be used to form superparamagnetic particles.

In some aspects, the shape of the particles can provide desired features. Particles can be provided in a wide variety of shapes, such as spherical, rod-shaped (nanorod), cubic, and other geometries. In some implementations, and as illustrated herein, particles are provided with a cubic shape. Particles can also be provided with a face-centered or body-centered crystal structure.

In general, a particle-generating process can proceed as follows. Target atoms can be ejected from one or more targets due to bombardment of ions (e.g., Argon ions) which can be generated by ionization of gas (e.g., a supplied sputtering gas). The sputtered atoms form an atom gas, and the gas condenses to form particles. The formed particles can be carried with a carrier gas and deposited on any suitable substrate. Optionally, one or more magnets can create magnetic fields around each target, controlling the formation of the particles. The carrier gas can also function as a cooling gas. More particularly, systems can use gas phase condensation techniques based on one or more sputtering sources to fabricate several kinds of particles, including, but not limited to, particles containing a metal. In some aspects, the metal may be any one of iron, cobalt, gold, silver, zirconium, to name a few examples. In some implementations, gas phase condensation techniques can be used to fabricate heterostructured particles such as FeCo, FeCo—FeCoO, FeCo—MgO, Fe—MgO, FeCo—ZnO, Fe—ZnO, FeZn, FeCo—Au, FeCo—Ag, FeCo—$SiO_2$, FeCo—$TiO_2$, Fe—Ag, Co—Au, C, and Fe—Au, Fe—$TiO_2$, $Fe_5Si_3$, $Fe_3Si$, $Fe_{16}N_2$, FeN, $FeSi_3$—Au, $Fe_5Si_3$—$SiO_2$, $Fe_5Si_3$—Au, $Fe_{16}N_2$—Fe(N), $Fe_{16}C_2$, $Fe_{16}C_2$—Au, $Fe_{16}N_2$—Au, $Fe_{16}N_2$—Ag, $Fe_{16}N_2$—$Al_2O_3$, $Fe_{16}N_2$—$TiO_2$, or $Fe_{16}N_2$—$SiO_2$. to name a few examples.

Exemplary particle deposition systems are described herein for purposes of illustrating inventive concepts. However, it will be readily appreciated that functionalized particles can be generated using other similar gas phase condensation techniques, or particle generating techniques such as thermal evaporation, ion beam and or electron beam.

FIG. 1 shows a cross-sectional view of an exemplary system 100 that can be used for spray functionalization of nanoparticles. A chamber 102 includes one or more sputtering targets 104. The target can be contacted by a sputtering gas (e.g., Argon) from a gas inlet 106. In some implementations, the system can include a soft iron ring and/or cone 108. The chamber can be cooled by a fluid (e.g., water) provided through a fluid inlet 110.

In operation, an ion current 112 (e.g., of $Ar^+$ ions) can be generated. As a result, nucleation can take place, for example generally within an area 114. Optionally, the generated nanoparticles can undergo growth in the chamber 102, for example in an area 116. Nanoparticles can exit the chamber 102, for example through one or more orifices 118.

The system 100 can include one or more sprayers 120, here placed in connection with the orifice 118. The sprayer can include any suitable spraying equipment, for example a nozzle connected to a pressurized container. Here a mist of one or more types of functional molecules is provided through one or more inlets 122. Accordingly, the nanoparticles can travel through the mist (e.g., a plasma) for some or all of their path after being generated. This can allow the nanoparticles and the coating material to react with each other and functionalize the nanoparticles. For example, the nanoparticles can be coated with one or more functional layers. The travel of nanoparticles can generally be brought about by removing gas through an outlet 124, for example by a vacuum pump.

The system 100 can include a substrate 126 for receiving some or all of the nanoparticles. Any suitable material can be used for the substrate, including, but not limited to, polymer, metal, and/or glass. Optionally, the substrate can be pre-coated with certain materials, including, but not limited to, small or large molecules for further modifying the nanoparticles. Accordingly, a layer 128 of surface-modified nanoparticles can be formed on the substrate. For example, the nanoparticles so deposited may have a particular functionalization depending upon the coating material sprayed onto the nanoparticles and/or the coating material provided on the substrate 126.

In operation, a gas (e.g., argon) can be introduced into the chamber 102 (e.g., a vacuum chamber). The gas can be ionized and pass through a plasma region (e.g., nanoparticle-forming region) that is formed by a hollow region of the target. For example, positively-charged ions in the gas can be accelerated by a negative potential at the target and knock out the atoms of the target, leading to the formation of atom gas. Then the atom gas can condense to form nanoparticles. The nucleation, formation and growth of the nanoparticles can be carried out in the thermal environment of the plasma. "Plasma" can refer to the gas that contains formed nanoparticles. A magnetic field can serve to control the movement of the positively-charged ions and the nucleation, formation and growth of the nanoparticles. As a result, erosion of the outside of the target, such as at an outlet end of the target, can be minimized.

In some implementations, the strength of the magnetic field (or H-field) can be in the range of 970 to 2000 Oe and can depend, for example, on the requirement of particle growth condition. Magnet selection can also depend on the particle size that is desired for the formed particles. Longer targets can increase the crystallization time and produce larger particles. Thicker magnets can increase the growth time and produce larger particles.

Figure 2:
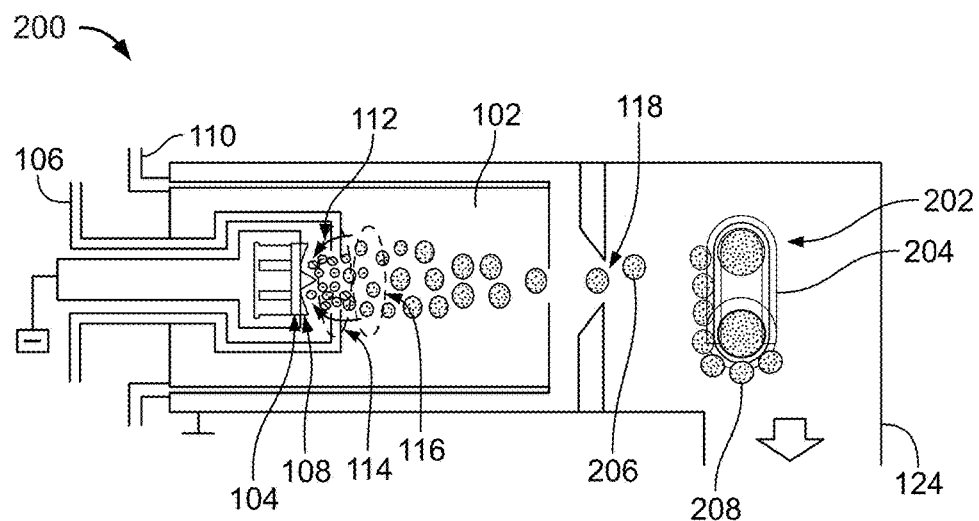
FIG. 2 shows an example of a system that can be used for continuous or stepped interval collection functionalization of particles.

FIG. 2 shows an example of a system 200 that can be used for a continuous or stepped-interval functionalization of nanoparticles. Similar to the example above, the system here includes the chamber 102 and the sputtering target 104, the inlets 106 and 110, the orifice 118, and, optionally the soft iron ring and/or cone 108. In operation, the ion current 114 can be generated, leading to nucleation in the area 114 and nanoparticle growth in the area 116.

In the system 200, a substrate 202 is arranged in connection with the orifice 118. Before nanoparticle generation begins, the substrate is coated with at least one coating layer 204. The coating layer can include one or more polymers to be provided as a functionalization coating on the nanoparticles.

In some aspects, the substrate 202 can have any suitable form that provides a surface for collection and functionalization of generated nanoparticles. The substrate 202 can be in a form that is easily removed from the system 200. The substrate 202 can be rigid or flexible, as desired. For example, in some aspects, the substrate 202 can comprise a plate, platform or other planar surface. In other aspects, a flexible substrate 202 can be provided in the form of a tape, film, or sheet, and can be coated with the polymer(s). In operation, generated nanoparticles 206, which have not yet been exposed to an environment outside the system 200, are collected on the substrate 202, forming collected nanoparticles 208. For example, the collection can occur due to the presence of a thin film of a desired coating material 204 on the substrate 202. In some implementations, a single layer deposition of particles can be obtained. In some implementations, single layer deposition and direct functionalization of particles can be achieved.

Substrate 202 thus includes a coating material 204 on a surface. The coating material 204 can comprise one or more polymers. In some aspects, suitable polymer is inert and/or nontoxic. Polymer can be substituted or unsubstituted. The polymer can include one or more functional groups for bonding to the particle surface and, optionally, to another compound.

When two or more polymers are included in the coating material 204, the coating can be referred to as a mixed matrix. For example, a mixed matrix may comprise a functionalization polymer for binding to the nanoparticle core, admixed with a non-reactive polymer. This can provide advantages, for example, when it is desired to dilute the amount of functionalization polymer provided on the substrate 202 and/or when the presence of a non-reactive polymer can provide enhanced properties such as solubility (and thus improved coating on the nanoparticles) of the mixed matrix. In some implementations, a mixed matrix can enhance control of size growth of the functionalized particles. In these aspects, the mixed matrix can help limit crosslinking of polymers in the shell portion of the functionalized particles.

Suitable polymers for use in accordance with inventive concepts include virtually any polymer that includes, or can be modified to include, a functional group for attachment to particle surfaces. Polymers can be selected to provide desired features to a particle surface, such as amount of coverage (e.g., passivation), hydrophilic or hydrophobic character, surface charge, and the like. Illustrative polymers include, but are not limited to, vinyl polymers, fatty acids, polyethers, polyesters, acrylic polymers, and aromatic polymers.

Illustrative vinyl polymers include polystyrene (($C_8H_8$)$_n$), polyvinyl alcohol (PVA, [$CH_2CH(OH)$]$_n$), polyethylene (such as PEG (H—(O—$CH_2CH_2$)$_n$—OH) or polyethyleneimine (PEI)), poly(methylidene malonate), polyvinylpyrrolidone (PVP), polypropylene, polyvinyl chloride (PVC) polyisobutylene, poly(methyl methacrylate), polytetrafluoroethylene (PTFE), polystyrene, polyvinyl acetate, polyvinyl sulfide, and the like.

Suitable fatty acids can be unsaturated or saturated. Illustrative unsaturated fatty acids include, but are not limited to, oleic acid, linoleic acid, myristoleic acid, palmitoleic acid, sapienic acid, elaidic acid, vaccenic acid, linoelaidic acid, α-linolenic acid, arachidonic acid, eicosapentaenoic acid, erucic acid, docosahexaenoic acid, and the like. Illustrative saturated fatty acids include, but are not limited to, caprylic acid, capric acid, lauric acid, myristic acid, palmitic acid, stearic acid, arachidic acid, behenic acid, lignoceric acid, cerotic acid, and the like.

Suitable polyethers can include, for example, PEG, polypropylene glycol (PPG), paraformaldehyde, polytetramethylene glycol (PTMG), polytetramethylene ether glycol (PTMEG), polyoxymethylene (POM), polyethylene oxide (PEO), polyoxyethylene (POE), polypropylene oxide (PPO), polyoxypropylene (POP), polytetrahydrofuran (PTHF), or aromatic polyethers such as polyphenyl ether (PPE) or poly(p-phenylene oxide) (PPO).

Suitable polyesters include poly(lactic acid), poly(glycolic acid), poly(ϵ-caprolactone), and their copolymers.

Illustrative acrylic polymers can include, for example, acrylates, methacrylates, acrylamides, acrylate-acrylamide, and any suitable polymer including the acryloyl group.

Illustrative aromatic polymers include poly(pyrrole), poly(aniline). Other suitable polymers include poly(alkylcyanoacrylates).

Block copolymers are also contemplated.

In some aspects, the polymer includes a functional group that is selected to interact with the surface of the particles to form a bond. In some implementations, the first functional group is a moiety that is capable of donating electrons to the particle surface, thereby forming a bond between the polymer and the particle surface. For example, in some embodiments, the polymer can include a first functional group such as hydroxyl (—OH), carboxyl (—COOH), thiol (—SH), phosphate (—$PO_4^{3-}$), sulfate (—$SO_4^{2-}$), aldehyde (—CHO), sulfide ($S^{2-}$), or the like, which functional group is capable of binding metal particles. Such functional groups can be terminal or internal functional groups.

In some aspects, the polymer can comprise a bifunctional polymer that includes a first functional group and a second functional group. The bifunctional polymer can be hetero-bifunctional (first functional group and second functional groups are different). In these aspects, the second functional group can be selected to interact with a compound of interest. Optionally, the polymer can be monobifunctional (first functional group and second functional group are the same). These embodiments can be useful, for example, when crosslinking of the particle coating is desired.

The length of the polymer chain can be selected to provide desired features to the particles. Polymer chains can be short or long. The polymer can be linear or branched. For example, long chain polymers can be used when it is desirable to provide functionalization coatings that can entangle each other, thereby providing clustered functionalized particles. One illustration of these aspects can be found in Example 4.

In operation, generated nanoparticles 206, which have not yet been exposed to an environment outside the system 200, travel toward the substrate 202 at a certain velocity. The nanoparticles 206 impinge upon the coating material 204 and become at least partially embedded into the coating material. Upon contacting the coating material, the particle surface reacts with functional groups of the coating material, and bonds are formed between the coating material and nanoparticle surface.

In some implementations, for example, nanoparticles 206 can comprise FeCo. The FeCo nanoparticles provide a pristine surface that readily reacts with functional groups (such as carboxyl groups and others described herein), to form a stable bond. The result is formation of functionalized nanoparticles composed of a magnetic core and a stable functionalization coating. The functionalized nanoparticles are thus stably bound to the functionalization coating, yet removably associated with the substrate 202. By removably associated is meant the particles are disposed on a substrate surface in a manner such that they can be removed by such methods as washing or dissolving the substrate material. The functionalized nanoparticles can subsequently be removed from the support by dissolving the substrate 202 in a suitable solvent, or by washing the nanoparticles from the substrate surface.

In some implementations, covalent bonding between the metal atoms from the surfaces of metallic particles and the H, or N, or P or C or F or Si or S or F or B or Al or Ga or Ge or Zn or Mg atoms from the pre-coated substrate polymer or biomolecule can occur and will inhibit or prevent the oxidation of those metallic particles when they are taken out the vacuum chamber.

In some implementations, ionic bonding between the atoms from the surfaces of particles and the O, or S or F or Cl or Li or Na or K or Be or Mg or Ca or Fe atoms from the pre-coated substrate polymer or biomolecule can occur and will inhibit or prevent the degradation of properties of those particles when they are taken out the vacuum chamber.

In further embodiments, the pre-coated substrate polymer can bond the particles through van der Waals force.

The thickness of coating material provided 204 on the substrate 202 can be controlled to fall within a useful range. For example, nanoparticles exit chamber 102 with a certain velocity. The coating material 204 can be provided with sufficient thickness to prevent or minimize reaction between the nanoparticle surface and the surface of support for the coating material, 202. At the same time, the coating material should not be so thick that excess coating material is utilized. In some aspects, excess (unbound) coating material should be washed from the surface of nanoparticles during later processing steps.

In some implementations, the substrate 204 comprises a roll of material. For example, the roll can be unwound from a spool to allow continuous exposure of new substrate surface to the nanoparticle trajectories. The substrate can be unwound by continuously winding the substrate onto another spool, for example. In some implementations, the substrate is a continuous loop that can be advanced so that new substrate areas face the nanoparticles.

Figure 3:
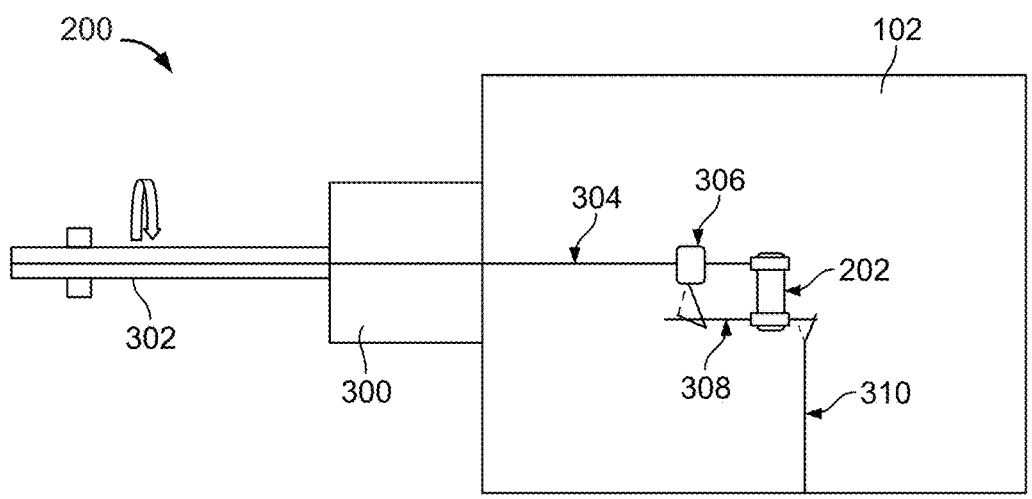
FIG. 3 shows another view of the system in FIG. 2.

FIG. 3 shows another view of the system 200 in FIG. 2. Here, the chamber 102 is placed in connection with a load lock chamber 300 which in turn has a motorized transfer 302 (e.g., a rotating shaft). A rotating rod 304 is connected to the motorized transfer 302 and extends through the load lock chamber 300 into the chamber 102, where it is provided with a bearing 306. For example, the bearing facilitates that the rotating rod can rotate in either or both directions.

On the rotating rod 304 is provided one of the spools that carries the substrate 202. For example, the rod can extend axially at least partway into the spool and can facilitate rotation of that spool. Another spool for the substrate has a supporting reel 308 which allows it to rotate. For example, the driving motion from the motorized transfer 302 can be transferred to one of the spools, and the movement of the substrate can then cause the supporting reel 308 to rotate. The supporting reel can have a fixture 310 for support, for example.

In accordance with inventive concepts, methods provide functionalized particles having a metal core and a coating layer, the coating layer comprising at least one polymer, wherein the polymer is bound directly to the surface of the metal core (for example, via covalent, van der Waals', or ionic bonds). As used herein, the term "layer" or "coating layer" refers to a layer of one or more coated materials of sufficient dimensions (for example, thickness and area) for its intended use over the entire, or less than the entire, portion of a particle surface. In some aspects, the coating layer is provided on a sufficient portion of the particle surface to inhibit or prevent oxidation of particles.

Some implementations involve methods and processes for directly functionalizing particles. For example, a one-step process can be performed in a vacuum or ultra high vacuum (UHV) chamber. In terms of example motivations for such implementations, there are various applications that require particles to be dispersed in a solution. Such applications include, but are not limited to, biomedicine, magnetic resonance imaging (MRI), hyperthermia, biomarker detection, cell separation, drug delivery, catalysis, plasmon resonance and recording media, to name just a few. Chemical synthesis has established relatively mature procedures for making a dispersion of particles, but not particles synthesized by physical methods.

Any of several different types of particles can be used. Examples include, but are not limited to, metal particles, magnetic particles, ferrite oxides, metallic alloys and semiconductors.

For example, production of particles containing Fe or FeCo in a vacuum environment can result in a particle surface with a high affinity for oxygen, nitrogen, or other elements that may contaminate the surface when the particles are removed from the vacuum and exposed to the atmosphere. The surface state of metallic particles gradually changes after they are removed from a vacuum environment. Particles easily form agglomerations or aggregations when they are exposed to an aqueous environment. Particles can sometimes form an agglomeration in a vacuum due to dense packing. Such agglomerations or assemblies may be undesirable in some applications, for example, when individual particles of a selected size are important for an application, and/or when the size of particles is critical to an application.

In some implementations, inventive concepts can be used to form functionalized particle assemblies. These assemblies can be formed inside the vacuum environment and can be coated as a unit with functionalization polymer. Such assemblies can be advantageous, for example, to achieve a larger overall particle size, to increase magnetic properties (when magnetic material is used), to provide a higher amount of a selected compound, etc.

Figure 9:
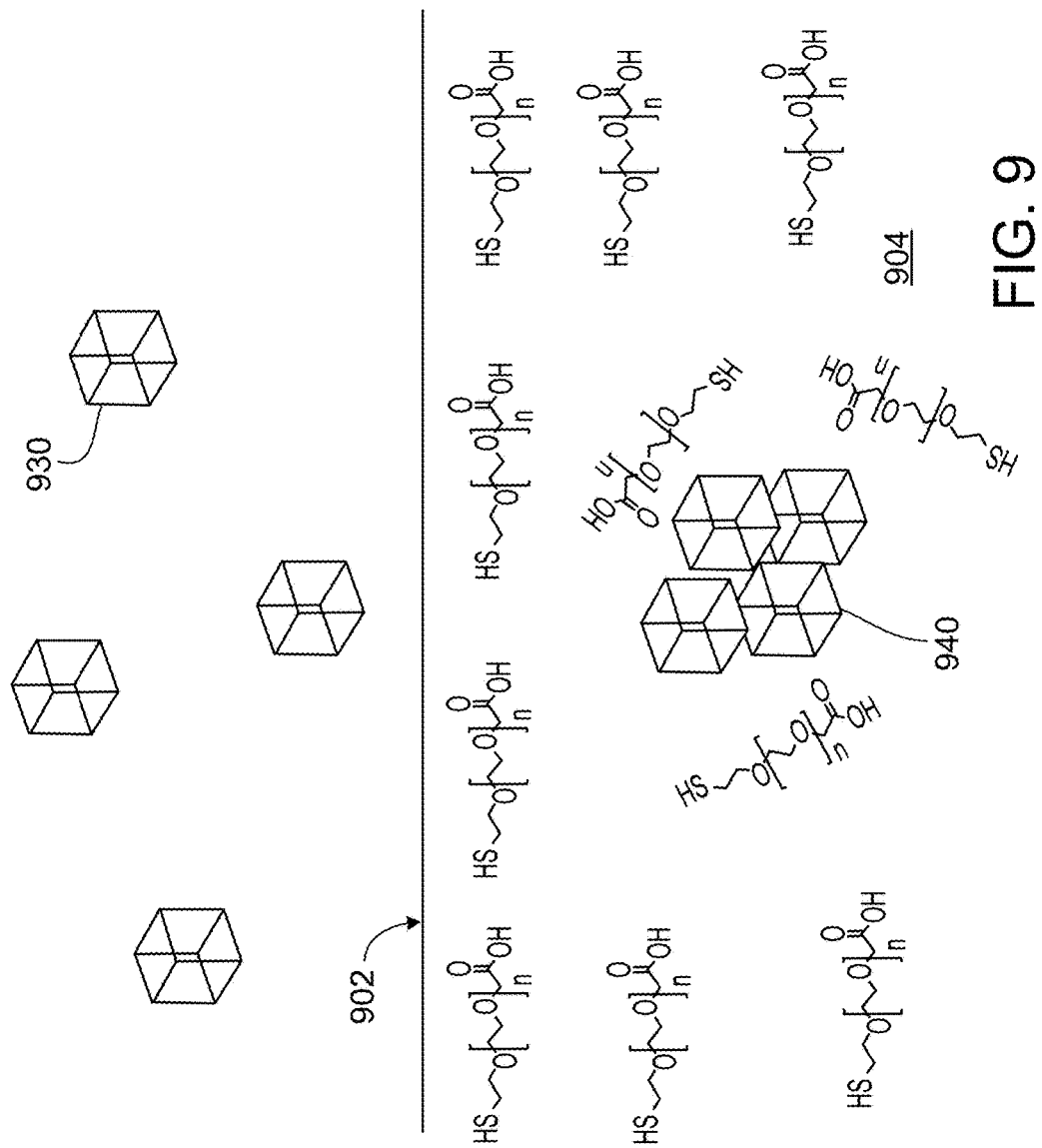
FIG. 9 is a schematic representation of particle cluster formation on a substrate surface.

In some embodiments, particles can form particle assemblies once they have contacted the collection substrate. One implementation of these embodiments is illustrated in FIG. 9. As shown, generated particles 930 can approach the substrate 902 as individual units. The substrate 902 is provided with a coating material 904 (in this case, heterobifunctional PEG, carboxyl-PEG-thiol). Once the particles contact the substrate 902, they can migrate to form clusters or assemblies 940. For example, if particles are hot enough when they impinge upon the substrate, the particles may migrate on the collection device and form particle assemblies. Factors that may influence particle assembly formation on the collection substrate can include, for example, the energy of the particles, charge, and selection of the polymer on the substrate surface. Temperature of the vacuum system and/or the particle collection device can be controlled to either encourage or discourage formation of particle assemblies, as desired. Features of the polymer that can be manipulated to impact formation of particle assemblies can include, for example, the size of polymer molecules, temperature sensitivity of the polymer, and the like.

Figure 10:
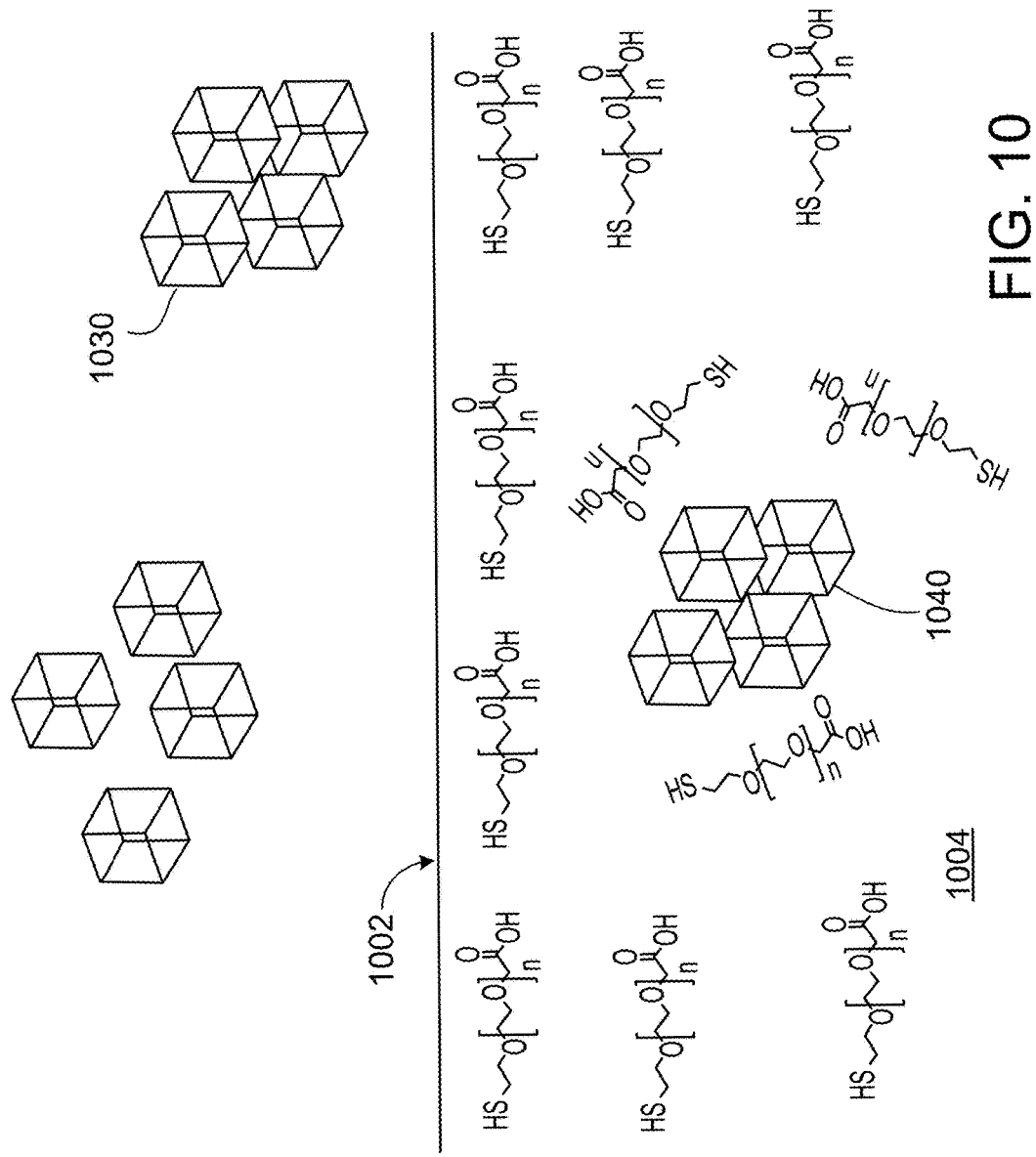
FIG. 10 is a schematic representation of particle assembly cluster formation before particles are deposited onto a substrate surface.

In some implementations, particles can form particle assemblies during the deposition process. One embodiment is illustrated in FIG. 10. As shown, generated nanoparticles 1030 can form particle assemblies 1040 before contacting the substrate 1002 of the collection device. The substrate 1002 includes a coating material 1004 (here shown as heterobifunctional PEG) for functionalization of the particle assemblies 1040.

In these aspects, it is the formed particle assemblies 940 and 1040 that form bonds, and become functionalized with, the functionalization coating.

In some implementations, particles (e.g., metallic) deposited from a deposition source in a vacuum environment can be surface modified in-situ and collected. For example, the modification process can involve spraying the coating material to form a cloud or aerosol of molecules through which particles travel and with which they react. As another example, the particles can be collected on a substrate that is coated with a thin film of the desired coating material. The molecular structure of a desired coating material can contain a functional group that is covalently bonded to the atoms on the surface of the particle. The coating material can contain one or more additional functional groups to make a surface that is directly usable for an application. Exemplary chemical groups that can form a bond with metal particles include, but are not limited to, COOH and —OH. Exemplary chemical groups that can form a bond with particles having an Au surface include, but are not limited to, —SH and —$NH_2$.

Optionally, the polymer can include a second functional group capable of binding compounds to the particle. In accordance with these aspects, the functionalized particle can provide a customizable magnetic particle that can be tailored to a particular application by coupling a selected compound to the second functional group. The selection of the particular compound is thus left to an end user. Illustrative compounds that can bind to this second functional group can include, but are not limited to, small molecules, proteins, nucleic acids, targeting ligands, peptides, antibodies, antibody fragments, detectable moieties, bioactive agents (such as drugs), imaging agents, and the like. Compounds reactive with (or capable of being modified to react with) the second functional group presented by the functionalization polymer can be used in accordance with inventive principles.

Suitable imaging agents include, but are not limited to, radiolabels for PET imaging and diagnostic agents suitable for MRI imaging (such as gadolinium), coumarin-6, rhodamine derivatives, DSB5491, cy5.5, surface enhanced raman spectroscopy (SERS) reagents, such as—mercaptopyridine, and the like.

In some implementations, the functionalized particle can be coupled to a visually or otherwise detectable moiety, for example, a chromophore or fluorophore.

As used herein, the term "peptide" refers to a sequence of 2 to 25 amino acids or peptidyl residues.

As used herein, a "bioactive agent" refers to an inorganic or organic molecule, which can be synthetic or naturally occurring, that causes a biological effect when administered in vivo to an animal, including but not limited to humans. Bioactive agents include macromolecules (i.e., molecules with a molecular weight of at least about 1000 Da) such as peptides, proteins, carbohydrates, nucleic acids, lipids, polysaccharides or combinations thereof; or organic or inorganic molecules. Illustrative bioactive agents are described below. A comprehensive listing of bioactive agents can be found in The Merck Index, Fourteenth Edition, Merck & Co. (2006).

Inventive particles can include one or more bioactive agents falling within one or more classes that include, but are not limited to: ACE inhibitors, actin inhibitors, analgesics, anesthetics, anti-hypertensives, anti polymerases, antisecretory agents, anti-AIDS substances, antibiotics, anticancer substances, anti-cholinergics, anti-coagulants, anticonvulsants, anti-depressants, anti-emetics, antifungals, antimicrobials, anti-glaucoma solutes, antihistamines, antihypertensive agents, anti-inflammatory agents (such as NSAIDs), anti metabolites, antimitotics, antioxidizing agents, anti-parasite and/or anti-Parkinson substances, antiproliferatives (including antiangiogenesis agents), anti-protozoal solutes, anti-psychotic substances, anti-pyretics, antiseptics, anti-spasmodics, antiviral agents, calcium channel blockers, cell response modifiers, chelators, chemotherapeutic agents, dopamine agonists, extracellular matrix components, fibrinolytic agents, free radical scavengers, growth hormone antagonists, hypnotics, immunomodulators, including immunosuppressants and corticosteroids, immunotoxins, inhibitors of surface glycoprotein receptors, microtubule inhibitors, miotics, muscle contractants, muscle relaxants, neurotoxins, neurotransmitters, polynucleotides and derivatives thereof, opioids, photodynamic therapy agents, prostaglandins, remodeling inhibitors, statins, steroids, thrombolytic agents, tranquilizers, vasodilators, and vasospasm inhibitors.

The term "antimicrobial agent" as used herein means antibiotics, antiseptics, disinfectants and other synthetic moieties, and combinations thereof. Classes of antibiotics include tetracyclines, rifamycins, macrolides, penicillins, cephalosporins, other beta-lactam antibiotics, aminoglycosides, chloramphenicol, sufonamides, glycopeptides, quinolones, fusidic acid, trimethoprim, metronidazole, clindamycin, mupirocin, polyenes, azoles, and beta-lactam inhibitors. Additional examples of antibiotics that can be used include teicoplanin, azithromycin, clarithromycin, ofloxacin, lomefloxacin, norfloxacin, nalidixic acid, sparfloxacin, pefloxacin, amifloxacin, enoxacin, fleroxacin, temafloxacin, tosufloxacin, clinafloxacin, clavulanic acid, itraconazole, ketoconazole, and nystatin.

Antiseptics are recognized as substances that prevent or arrest the growth or action of microorganisms, generally in a nonspecific fashion, for example, by inhibiting their activity or destroying them. Examples of antiseptics include silver sulfadiazine, peracetic acid, sodium hypochlorite, phenols, phenolic compounds, iodophor compounds, quaternary ammonium compounds, and chlorine compounds. Additional examples of antiseptics and disinfectants include thymol, a-terpineol, methylisothiazolone, cetylpyridinium, chloroxylenol, hexachlorophene, cationic biguanides (i.e. chlorhexidine, cyclohexidine), methylene chloride, iodine and iodophores (i.e. povidone-iodine), triclosan, furan medical preparations (i.e. nitrofurantoin, nitrofurazone), methenamine, aldehydes (glutaraldehyde, formaldehyde) and alcohols. Other examples of antiseptics and disinfectants will readily suggest themselves to those of ordinary skill in the art.

Anti-viral agents are substances capable of destroying or suppressing the replication of viruses. Examples of anti-viral agents include .alpha.-methyl-P-adamantane methylamine, hydroxy-ethoxymethylguanine, adamantanamine, 5-iodo-2'-deoxyuridine, trifluorothymidine, interferon, and adenine arabinoside.

Anti-pyretics are substances capable of relieving or reducing fever. Anti-inflammatory agents are substances capable of counteracting or suppressing inflammation. Examples of such agents include aspirin (salicylic acid), indomethacin, sodium indomethacin trihydrate, salicylamide, naproxen, colchicine, fenoprofen, sulindac, diflunisal, diclofenac, indoprofen and sodium salicylamide. Local anesthetics are substances that have an anesthetic effect in a localized region. Examples of such anesthetics include procaine, lidocaine, tetracaine and dibucaine.

In these aspects, inventive concepts provide a functionalized particle that is customizable. A user can further couple any desired compound to the functionalized particle. Illustrative compounds include catalytically active species, various bioactive agents (such as drugs), specific binding sites, or other functional groups. Such compounds can be selected by a user, based upon final application of the functionalized particles.

In some implementations, functionalized particles can be provided in a substantially dry form. For example, inventive concepts provide a particle composition comprising, in dry form, a substrate, a polymer layer on a surface of the substrate, and particles removably associated with a surface of the substrate, wherein the particles are functionalized by polymer molecules present within the polymer layer.

By "dry form" is meant a form of the functionalized particles where it is essentially dry, i.e., it is not dissolved in a liquid composition, such as aqueous composition. Dry form does not however mean that the functionalized particles are completely dry, i.e., entirely free of liquids. The functionalized particles (or the polymer layer on a surface of the substrate) may absorb small amounts of water from the surrounding environment. Thus, functionalized particles in dry form may contain up to 10% (w/w) water, such as 8% or 6% or 5% or 4% or 3% or 2% or 1% (w/w) water.

The dry form may be stored under appropriate conditions (such as ambient conditions) for extended periods of time, until desired use. In some implementations, functionalized particle kits in dry form can be provided in a suitable container such as a bottle, vial or ampoule. Other optional components of the kit can include, for example, an aqueous solution for dispersing the particles and thus in situ preparing an aqueous dispersion in either water or in a buffer solution of appropriate pH, syringe for application or injection of the dispersion, a magnet for separation or isolation of metal particles, additional reagents for subsequent reactions, and the like.

Thus, in some embodiments, kits are provided that comprise one or more of: functionalized particle in dry form, one or more dispersion solutions, washing solutions, coupling solutions, syringe, magnet, and additional reagents. In some embodiments, a solution of the kit is a buffer. For example, kits are provided for cell separation that include one or more of: functionalized particle in dry form, aqueous solution for dispersing particles, magnet, and additional reagents such as cell specific targeting ligands. In another example, kits are provided for MRI that include one or more of the following: functionalized particles in dry form, aqueous solution for dispersing particles, and loading reagent (such as a lipid-containing reagent).

Particles in a dry form can provide advantages, such as extended stability.

In some aspects, inventive concepts provide an aqueous dispersion of functionalized particles, dispersed in water or in a buffer at a suitable range of pH (for example, in a range of about 4.5 to about 8, or in a physiological buffer at pH in a range of about 7.3 to 7.4). The particular pH of the buffer can be determined based upon such factors as the functionalization layer provided on the particle core and the desired application for the particles (for example, administration to a patient, in vitro analytical methods, and the like).

According to some aspects, an aqueous dispersion of functionalized particles can be obtained by dissolving the substrate in water or a suitable solvent. After dissolution of the substrate, functionalized particles can optionally be washed to remove excess, unbound polymer from the functionalized particles.

The aqueous solution dispersing the functionalized particles or a pharmaceutical composition comprising the same may include additional components as long as the components are compatible with the dispersion, wherein "compatible" is to be understood as for example components that do not cause precipitation or do not cause aggregation of the particles.

Thus, inventive concepts provide kits including one or more of the following: a dispersion of functionalized particles, a compound such as small molecules, proteins, nucleic acids, targeting ligands, peptides, antibodies, antibody fragments, detectable moieties, bioactive agents (such as drugs), imaging agents, and the like.

In some embodiments, kits can comprise a pharmaceutical composition comprising a functionalized particle and a pharmaceutically acceptable carrier. In some implementations, pharmaceutical compositions and formulations may include sterile aqueous solutions which may also comprise at least one of pharmaceutically acceptable additives such as, but not limited to, penetration enhancers, carrier compounds, buffers, stabilizers, diluents or other pharmaceutically acceptable carriers or excipients.

Functionalized particles in accordance with inventive concepts can provide improved stability over metal particles produced according to prior methods. The "stability" in the context of the present disclosure may be determined by various chemical and/or physical methods, and is to be taken to mean that no significant formation of aggregates or precipitation of the functionalized particles is observed. In some embodiments, "stability" can be directed to the preservation of the small size (such as nano- or micro-) of the particles.

Inventive particles and compositions can be formulated as pharmaceutical compositions and administered to a mammalian host, such as a human patient in a variety of forms adapted to the chosen route of administration (for example, parenterally, by intravenous, intramuscular, topical or subcutaneous routes).

In some aspects, inventive particles can be systemically administered, in combination with a pharmaceutically acceptable vehicle such as an inert diluent or a carrier. In addition, particles could be incorporated into sustained-release preparations and devices.

Particles can also be administered intravenously or intraperitoneally by infusion or injection. Dispersions of the inventive particles can be prepared in water, optionally mixed with a nontoxic surfactant or other diluent. Dispersions can also be prepared in glycerol, liquid PEGs, triacetin, and mixtures thereof and in oils.

Useful dosages of inventive particles can be determined by comparing their in vitro activity and in vivo activity in animal models. Methods for the extrapolation of effective dosages in mice (or other animals) to humans are known in the art. See, for example, U.S. Pat. No. 4,938,949.

In still further implementations, kits can comprise functionalized nanoparticles useful for MRI contrast. Such MRI contrast kits can include, for example, a functionalized particle in a dry form or in dispersion, as well as one or more optional components such as a compound for coupling to the functionalized particle, one or more reagents useful for MRI contrast (such as loading reagent and other lipid-containing reagents), stabilizers, diluents, and other suitable reagents.

Some implementations can provide any or all of the following advantages. The thin film of coating material on a substrate within the sputtering environment can provide a sufficient reserve to fully coat the surfaces of the deposited particles. When exposed to the atmosphere upon removal from the vacuum system, the surfaces of the particles may have been passivated to reduce or eliminate interaction with the atmosphere. A direct coating can prevent further change of the surface status of the particles. A direct coating process can simplify a manufacturing procedure, avoid loss of particles during an intermediate process, and/or save labor. A coating material can make the surface of particles terminated with a desired functional group for one or more particular applications.

Some implementations can involve a post-treatment of the functionalized nanoparticles inside the vacuum chamber. One example for this post-treatment is to heat the functionalized particles by collecting the particles on a heated substrate or using a radiation (e.g. lamp) type heater to heat the substrate indirectly. For those implementations, high temperature resistant polymer coating (e.g., polyurethanes, polyesters and polymers containing epoxy groups) can be desirable. In some aspects, a post-treatment process could improve the performances of particles and the bonding between the particles and polymer coating. For example, crystallinity of particles could be improved by heating up the as-prepared amorphous particles. For another example, ferromagnetic particles could be formed and well dispersed in the polymer matrix after post-annealing the as-prepared superparamagnetic nanoparticles within polymer matrix. For another example, Fe—N bonding could be enhanced through a post-annealing process by heating up the as-prepared Fe particles within polymer with N bonding sites. For another example, a UV radiation process could be used to refine the coating polymer around the as-prepared particles. In some implementations, heating the functionalization polymer during and/or after particles are collected can crosslink the polymers present in the functionalization layer.

In addition, inventive methods and systems can enlarge particles, change the surface chemistry of the particles, and provide attachment points for additional compounds. When desired, long chain polymers or dendrimers can be attached to the particle surface to agglomerate the particles.

Functionalized particles in accordance with inventive concepts can provide improved solubility in aqueous systems, improved stability, reduced toxicity, improved bioavailability (particularly when used to deliver therapeutic agents), and cost-effective production (even at larger industrial scale). Functionalized particles can allow the attachment of a wide variety of bioactive agents, which may further be used to deliver bioactive agents (such as drugs) or other substances, to a specific location within a patient. Thus, the novel functionalized particles can enable reduced toxicity and enhanced biological effect as compared to other metal containing particles.

In some implementations, particles can be generated by techniques other than sputtering. For example, thermal evaporation, ion beam and/or electron beam sources can also be used to generate atoms of a material that can in turn form particles. One of skill in the art will readily appreciate the techniques described herein can be adapted for these other particle generation systems.

Thus, in some implementations, a particle functionalization system comprises: a solid material source in a heating stage; a heating stage to evaporate the solid material and thereby cause release of atoms of the material; at least one magnet providing a magnetic field that controls movement of the atoms and electrons and nucleation, formation and growth of particles from the released atoms; and a particle collection device that collects particles and assemblies of particles, the collection device comprising a substrate and a polymeric functionalization coating disposed on the substrate, wherein particles impinge upon and form bonds with molecules of the functionalization coating.

In some implementations, a particle functionalization system comprises: a solid material source; a stand alone energies particle source such as an electron beam source or ion beam source, wherein the energies particle source causes release of atoms of the material; a potential that is applied to at least the target and that causes ions from the ionized gas to impact a surface of the target and release atoms of the material; at least one magnet providing a magnetic field that controls movement of the ions and electrons and nucleation, formation and growth of particles from the released atoms; and a particle collection device that collects particles and assemblies of particles, the collection device comprising a substrate and a polymeric functionalization coating disposed on the substrate, wherein particles impinge upon and form bonds with molecules of the functionalization coating.

EXAMPLES

Synthesis of Functionalized Superparamagnetic Nanoparticles

For Examples 1-3, nanoparticles were produced using deposition systems as described in PCT Application No. PCT/US2012/021269 ("Nanoparticle Deposition Systems," Wang, et al.).

For Examples 4-5, nanoparticles were producing using deposition systems as described in PCT Application No. PCT/US2014/14264 ("Multi-Surface Nanoparticle Sources and Deposition Systems," Wang et al.).

Characterization of Functionalized Superparamagnetic Nanoparticles.

The internal structure of superparamagnetic nanoparticles was determined by Transmission Electron Microscopy (TEM) measurements for which a dried sample was placed on a graphite-coated copper TEM grid.

Within Examples 4-6, nanoparticle structure and chemical composition were characterized by X-ray photoelectron spectroscopy/electron spectroscopy for chemical analysis (XPS/ESCA). XPS analysis was performed with a Physical Electronics Instruments (PHI) Quantum 2000 X-ray photoelectron spectrometer. Photoemission was stimulated by a monochromated Al Kα radiation (1486.6 eV). These methods allowed quantitative elemental and chemical bonding calculations to a depth of approximately 9 nm.

Example 1

Nanoparticle Deposition into a PVA Film

The sample collection substrate in this example was a preformed PVA film. Nanoparticles were generated using a sputtering system with a flow rate of 20 sccm (standard cubic centimeters per minute) 0.4 amps (230 Watts), and a sputtering duration of 1 minute.

Formed nanoparticles were carried by argon gas into the collection chamber and deposited on a substrate having a PVA film on its surface. After sufficient time had passed, the substrate containing PVA film and nanoparticles deposited into the PVA film was removed from the vacuum chamber.

Upon removal from the vacuum chamber, the PVA film with nanoparticles deposited within was dissolved into distilled water. As a control, a PVA film that did not contain nanoparticles was also dissolved into distilled water. The PVA film dissolved into water quickly and was completely dissolved into water after approximately 20 minutes. Solubility of the PVA film was not influenced by the presence of nanoparticles in the film.

Once dissolved into water, the resulting solution was characterized for nanoparticle stability. This stability was characterized by a response to a magnetic field and by the duration the nanoparticles could be suspended in a column of fluid. Nanoparticles that were modified with PVA by deposition into the film stayed suspended in the column of fluid for at least 60 minutes, were responsive to a permanent magnet applied after 15 minutes, and remained responsive to a magnetic field for extended periods of time after being dissolved. After sonication, the solution could still be re-dispersed and kept stable.

Results indicated that a PVA film can be a good medium for transferring particles into water. PVA film can be convenient to use, be vacuum compatible, and/or offer good stability of the particle solution. If desired, a PVA film can by synthesized to include one or more functional groups to allow subsequent reaction of the functionalized nanoparticles with additional ligands, as desired.

Example 2

Nanoparticle Deposition into an Oleic Acid Film

Nanoparticles were generated using a sputtering system as described in Example 1.

For this Example, a Mylar film was used as a substrate and was coated with oleic acid. Prior to coating the Mylar film support, the supports were cleaned using ethanol and isopropanol and subsequently dried. The oleic acid film was applied to the Mylar film using a Mayer rod which applied an even coating thickness. Oleic acid was provided in isopropanol at a concentration in the range of about 0.1 mg/mL to about 0.8 mg/mL. The oleic acid was applied as a mix with isopropanol, in different concentrations: 0.5 mg/mL oleic acid, 0.6 mg/mL, 0.7 mg/mL and 0.8 mg/mL. After the film was applied to the Mylar film support it was allowed to dry.

These samples then had nanoparticles deposited into them using a sputtering system at a flow rate of 20 sccm of Argon gas for a total exposure of 1 minute. After sputtering, the substrate containing oleic acid film and nanoparticles deposited into the oleic acid film was removed from the vacuum chamber.

Figure 4:
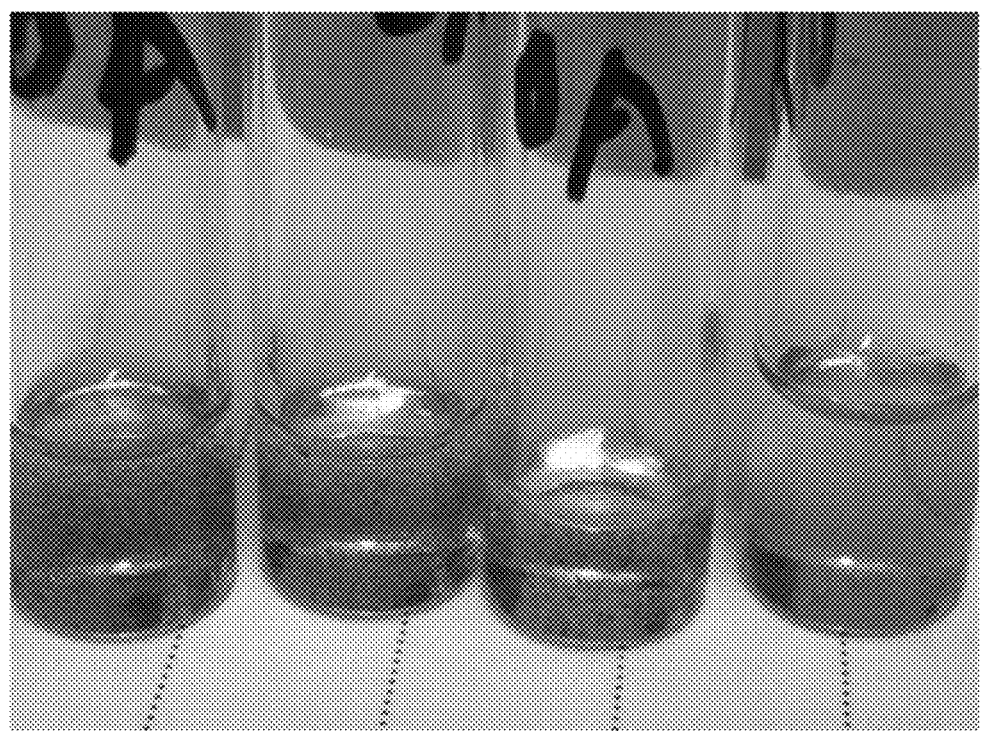
FIG. 4 is a photograph of FeCo nanoparticles functionalized with oleic acid and removed from a collection substrate by washing with chloroform.

After exposure the oleic acid nanoparticle layer was washed away from the Mylar film support using chloroform. Results of the suspension in chloroform are illustrated in FIG. 4. The structure of oleic acid allowed for a covalent bond to be formed with the nanoparticle. As a result the nanoparticles remained suspended in the solvent for a longer period of time relating to the concentration of oleic acid they were deposited into; 0.5 mg/mL oleic acid remained in solution the shortest time whereas the 0.8 mg/mL oleic acid remained in solution the longest time. The photographs of FIG. 4 were taken at three hours after washing the functionalized nanoparticles into the chloroform solution. In the photograph, concentration increases from left to right, beginning with 0.1 g/ml solution at the far left, progressing to 0.2 mg/ml, 0.3 mg/ml, and finally 0.4 mg/ml on the far right. Little to no apparent aggregates were observed at 3 hours. Thus, the sample with the highest oleic acid concentration showed better prevention of aggregation.

Accordingly, using oleic acid coating on Mylar film as substrates enabled transfer of nanoparticles into organic solvent. Results illustrated a high concentration of oleic acid and low concentration of particles can provide a stable solution, for example for 30 minutes to an hour.

Example 3

Nanoparticle Deposition into a 4 Branched Monofunctional PEG Film

A glass support was provided as substrate. The substrate was provided with a thin film of monofunctional carboxylic acid terminated 4-branched PEG mixed with unmodified PEG MW2000.

To prepare substrates, glass slides were first cleaned with ethanol and isopropanol, and subsequently dried. An amount of 0.2 ml PEG2000 solution was added to 0.8 ml of 4-arm-branched PEG-COOH. The solution was mixed uniformly, for example by vibrating it.

The PEG solution (400 µl) was applied to the glass substrate by spin coating (4000 rpm for 30 seconds). The final ratio of branched PEG to unbranched PEG was 4 to 1 in water. After application, the film was allowed to dry. The coated support was then placed into the vacuum system and nanoparticles were deposited into the sample as described in Example 1, with the modification that deposition was performed at an argon gas flow rate of 20 sccm for three cycles of 25 seconds each.

After deposition of nanoparticles was completed, samples were removed from the vacuum system. Nanoparticles were then removed from the glass support using distilled water and sonication. Once removed, the nanoparticles were characterized by determining how long the nanoparticles would stay suspended in solvent, in this case distilled water. Unmodified nanoparticles were used as a control. Results indicated that the nanoparticles remained suspended for hours in clear contrast to minutes for control. It was observed that nanoparticles stayed in the solvent for approximately 30 minutes before they began to aggregate.

The effect of heating substrates in situ was observed by heating substrates to a temperature of approximately 45° C. before taking the samples out of the collection chamber. Nanoparticles were removed from the substrates as described in this Example, using distilled water. A clear solution formed that was sustained for several hours. Aggregates were observed to form overnight.

Results indicated it is possible to transfer particles into water by using 4-arm-PEG-COOH coating on glass as substrates. A high concentration of 4-arm-PEG-COOH can be used. The —COOH group is a functional group and can be helpful for transferring particles into water.

Example 4

Nanoparticle deposition into a Carboxylic Acid modified Polystyrene Film

The substrate in this example comprised a thin film of mono-functional carboxylic acid modified polystyrene on an aluminum foil support.

The mono-functional polystyrene was applied to the foil support by drying down a 40 mg/mL polymer concentration in 2-butanone. The coated substrate was then placed into the vacuum chamber.

Nanoparticles were generated using a sputtering system with an argon gas flow rate of 305 sccm, an argon gas pressure of 12 mTorr, a sputtering current of 0.6 amps, and a sputtering duration of 5 minutes.

Formed nanoparticles were carried by argon gas and deposited on the aluminum substrate having a mono-functional styrene film on its surface. After sufficient time had passed, the substrate containing polystyrene film and nanoparticles deposited into the polymer film was removed from the vacuum chamber.

The sample was removed from the chamber and resuspended into 2-butanone. This sample was washed repeatedly by separating the nanoparticles from the solution using a magnetic field and removing the solvent. Then solvent was once again added and the nanoparticles released from the magnet and resuspended. This wash procedure was done three times. After washing to prepare the sample for analysis, the sample in solvent was poured onto aluminum foil and concentrated from the solvent using a magnet then allowed to dry.

Figure 5:
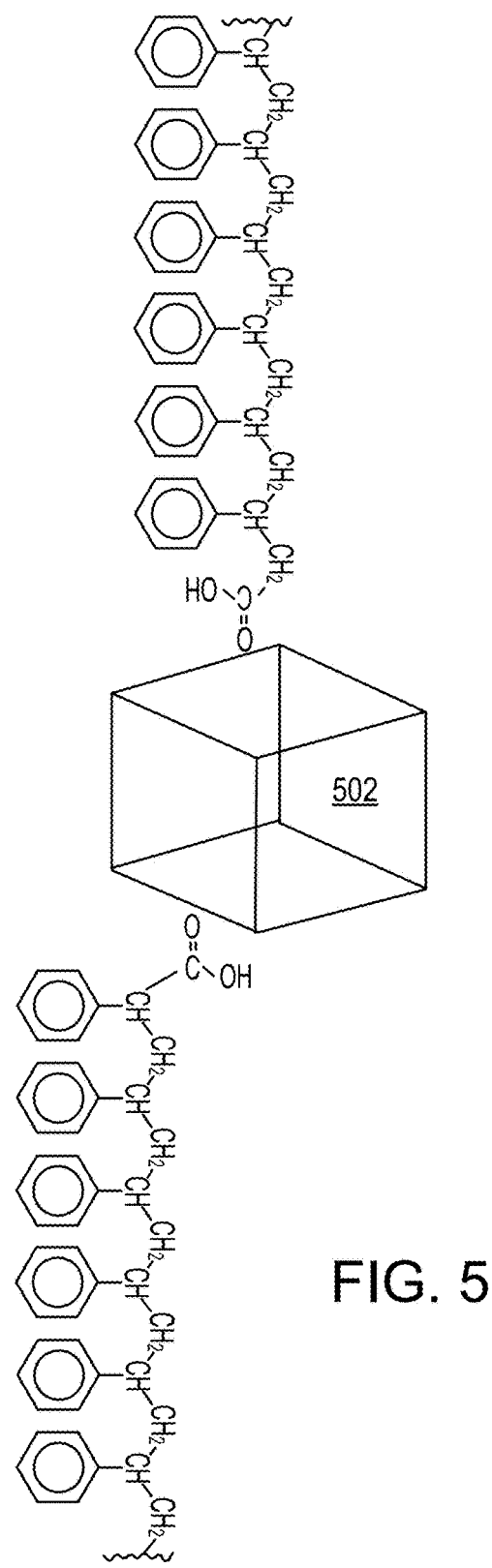
FIG. 5 is a schematic representation of nanoparticles functionalized with polystyrene.

Samples were analyzed by XPS/ESCA. FIG. 5 shows a schematic of the nanoparticle core 502 functionalized with polystyrene. As illustrated, the carboxyl group is oriented toward the nanoparticle 502. XPS measurement of the oxygen concentration in the carboxylic acid group compared to the iron plus cobalt concentration suggested that between one and two carboxylic acid polystyrene molecules are attached to each iron cobalt nanoparticle. The polystyrene molecule used in this example is a 200,000 repeat, estimated to be about 450 nm in length. Although the particle is shown having a cubic shape, particles can be provided in any suitable shape, such as spheroid, and the like.

The carbon—C1s—spectrum from this sample was consistent with polystyrene based upon the dominant hydrocarbon line. The C1s spectrum also included a very complex Shake-up structure fit with four bands by peak deconvolution. The Shake-up peaks in this spectrum indicated a strong metal-ligand bond between the carboxyl group and the iron cobalt nanoparticle. The deconvolved C1s spectrum included a C—O band and a smaller C=O band, indicative of the carboxyl group reacted with the FeCo nanoparticles. XPS peak binding energies also showed both cobalt and iron in the nanoparticle were oxidized. The O1s spectrum showed oxygen from the carboxylic acid structure. The binding energy and peak structure of the O1s peak was affected by the carboxyl group binding to the FeCo nanoparticle.

Elemental composition of the sample of FeCo nanoparticles attached to polystyrene is shown in Table 1. Table 2 shows fractional concentrations of the C1s peak determined by deconvolution. The C—C,H peak was from the polystyrene backbone. C—O is from the hydroxyl group within the carboxylic acid group, and C=O is the carboxyl group. The Shake-up Structure of the C1s peak was shifted to higher binding energies.

In Table 2, the carbon concentration of C—O should equal carbon in C=O considering the carboxylic acid structure. The shift of C=O associated carbon concentration to the Shake-up structure suggests that the strong ligand-metal bond involved the carboxyl group rather than the hydroxyl group.

The low measured concentration of iron and cobalt is due to a dense polymer covering of the nanoparticles and the escape depth of the photoelectrons, approximately 6 to 9 nm.

TABLE 1

| Sample | Atomic Concentrations (in %) | | | | | |
| --- | --- | --- | --- | --- | --- | --- |
| | C | N | O | S | Fe | Co |
| NP-polystyrene-solvent residue | 90.2 | — | 6.6 | — | 1.0 | 1.4 |

TABLE 2

| | Carbon Chemical States (in % of Total C) | | | | | | | |
|---|---|---|---|---|---|---|---|---|
| Sample | C—C,H | C—O | C=O | O—C=O | Shake-up 1 | Shake-up 2 | Shake-up 3 | Shake-up 4 |
| NP-polystyrene-solvent residue | 83 | 8 | 1 | — | 2 | 4 | 1 | 1 |

Figure 6:
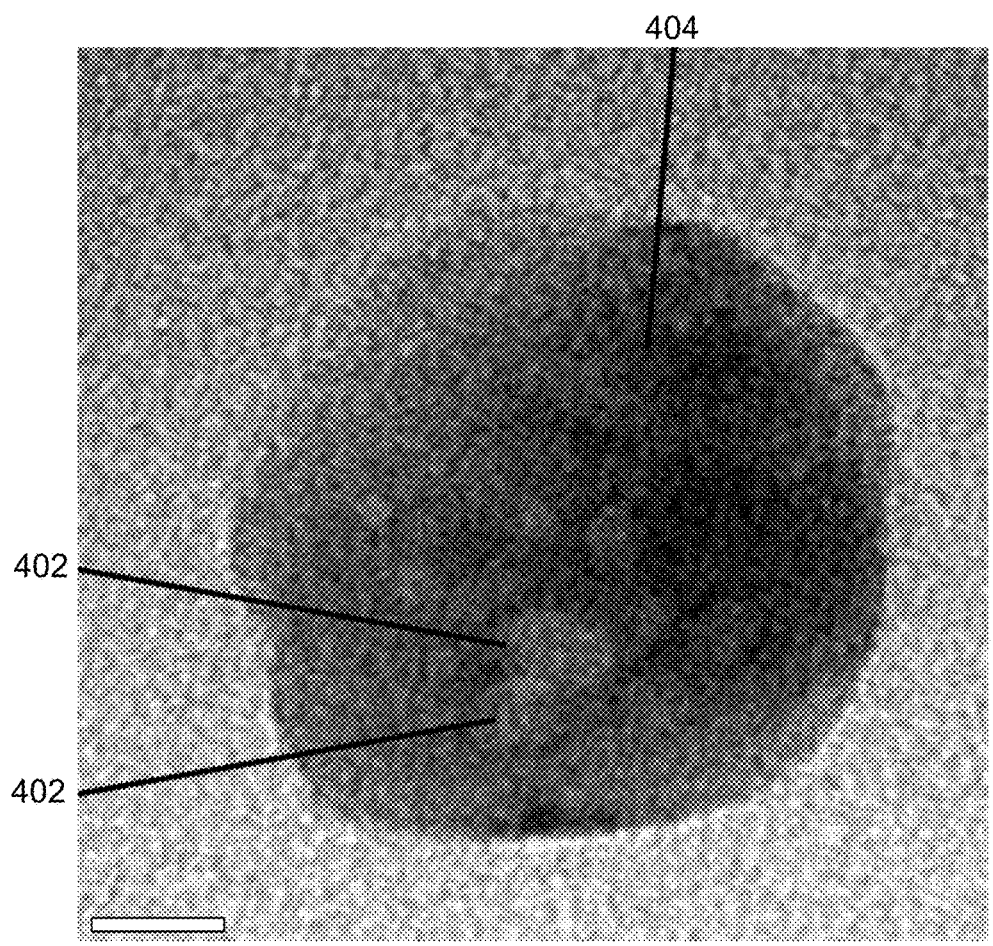
FIG. 6 is a transmission electron microscopy (TEM) image of several iron cobalt nanoparticles within an entanglement of polystyrene polymers; scale (left corner) is 10 nm.

The TEM image of FIG. 6 appears to show several nanoparticles that were magnetically responsive within an entanglement of polystyrene polymers. Particles are indicated at 402, while the darker area (404) shows a thicker polymer area. The diameter of the imaged nanoparticle/polymer structure was approximately 45 nm.

Example 5

Nanoparticle Deposition into a Heterobifunctional Carboxylic Acid-Thiol PEG Film Nanoparticles were prepared in an UHV system as described in Example 4.

The substrate in this example comprised a thin film of heterobifunctional carboxylic acid thiol PEG on an aluminum foil support. The heterobifunctional PEG was applied to the foil support by drying down a 20 mg/mL concentration of polymer in methanol. The sample was then placed into the vacuum chamber and nanoparticles were deposited into the coated substrate with an Argon gas flow rate of 305 sccm for 5 minutes.

The sample was removed from the UHV chamber and resuspended into methanol. The sample was then washed repeatedly by separating the nanoparticles from the solution using a magnetic field and removing the solvent. Then solvent was once again added and the nanoparticles released from the magnet and resuspended. This wash procedure was performed three times.

After washing to prepare the sample for analysis, the sample in solvent was poured onto aluminum foil and concentrated from the solvent using a magnet then allowed to dry.

Figure 7:
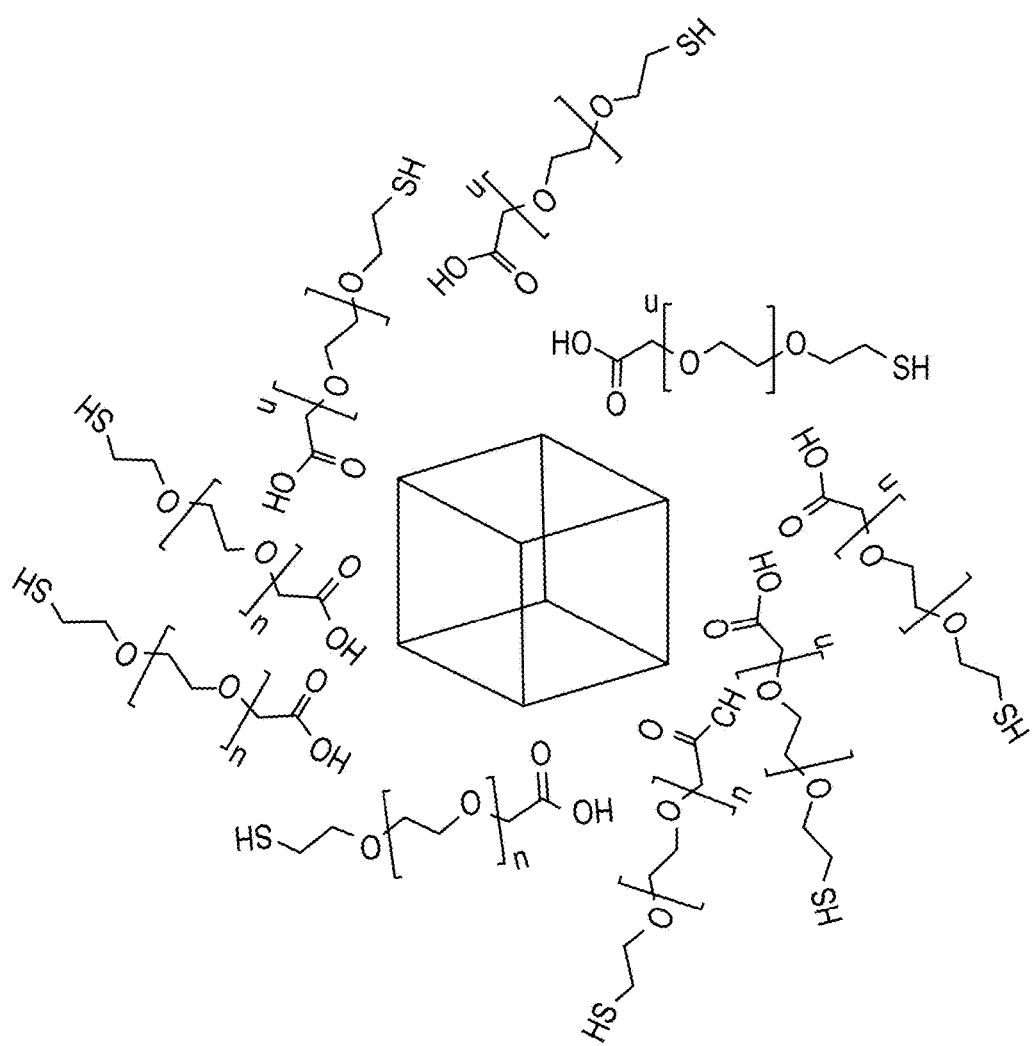
FIG. 7 is a schematic representation of a nanoparticle core functionalized with a heterobifunctional polyethylene glycol (PEG).

Samples were analyzed by XPS/ESCA. FIG. 7 shows a schematic of the nanoparticle core functionalized with carboxyl-PEG-thiol. As illustrated, the carboxyl group is oriented toward the nanoparticle. XPS measurement of the iron plus cobalt concentration suggested that a dense coating of carboxyl-PEG-thiol molecules were attached to each iron-cobalt nanoparticle. Steric hindrance may have prevented bonding of additional PEG molecules. The PEG molecule contained approximately 5000 repeat units and was estimated to be 35 nm in length. Approximately 2900 carboxyl-PEG-thiol molecules were available for each nanoparticle on a gram per gram ratio. Bonding of the PEG to the nanoparticle occurred through the carboxyl group.

Deconvolution of the C1s spectrum of FeCo nanoparticles-PEG showed the C—O peak was dominant, consistent with a PEG backbone. A small C—C,H peak was observed from the thiol group, and smaller C=O bands originated from the attached carboxylic acid group. XPS Peak binding energies indicated both Co and Fe in the nanoparticle core were oxidized.

The O1s spectrum showed oxygen in the PEG structure and carboxylic acid structures. Binding energy and Peak amplitude of the O1s C=O peak was affected by carboxyl group binding to the FeCo nanoparticle.

Table 3 shows elemental composition of the sample of FeCo nanoparticles attached to carboxylic acid-PEG-thiol. A low concentration of iron and cobalt illustrated that there was a dense polymer cover of the nanoparticles.

In Table 4, C1s peak deconvolution showed C—C,H and C—O predominantly from the PEG backbone. It is probable that the Shake-up structure was not apparent on this sample due to the dense polymer covering over the nanoparticles and the photoelectron escape depth of approximately 6 to 9 nm. Small impurities are not included in the table.

Sulfur peak deconvolution indicated three chemical forms, identified as sulfide, thiol and sulfate, possibly suggesting some sulfur bonding with the nanoparticles; however, thiol was present in the sample at approximately 0.8 atomic percent.

TABLE 4

| | Atomic Concentrations (in %) | | | | | |
|---|---|---|---|---|---|---|
| Sample | C | N | O | S | Fe | Co |
| NP-PEG | 61.6 | — | 34.5 | 0.3 | 0.2 | 0.5 |

TABLE 5

| | Carbon Chemical States (in % of Total C) | | | | | | | |
|---|---|---|---|---|---|---|---|---|
| Sample | C—C,H | C—O | C=O | O—C=O | Shake-up 1 | Shake-up 2 | Shake-up 3 | Shake-up 4 |
| NP-PEG | 10 | 87 | 3 | 0.5 | — | — | — | — |

TABLE 6

| | Sulfur Chemical States (in % of Total S). | | |
|---|---|---|---|
| Sample | Sulfide | Thiol | Sulfate |
| NP-PEG | 41 | 25 | 24 |

Figure 8:
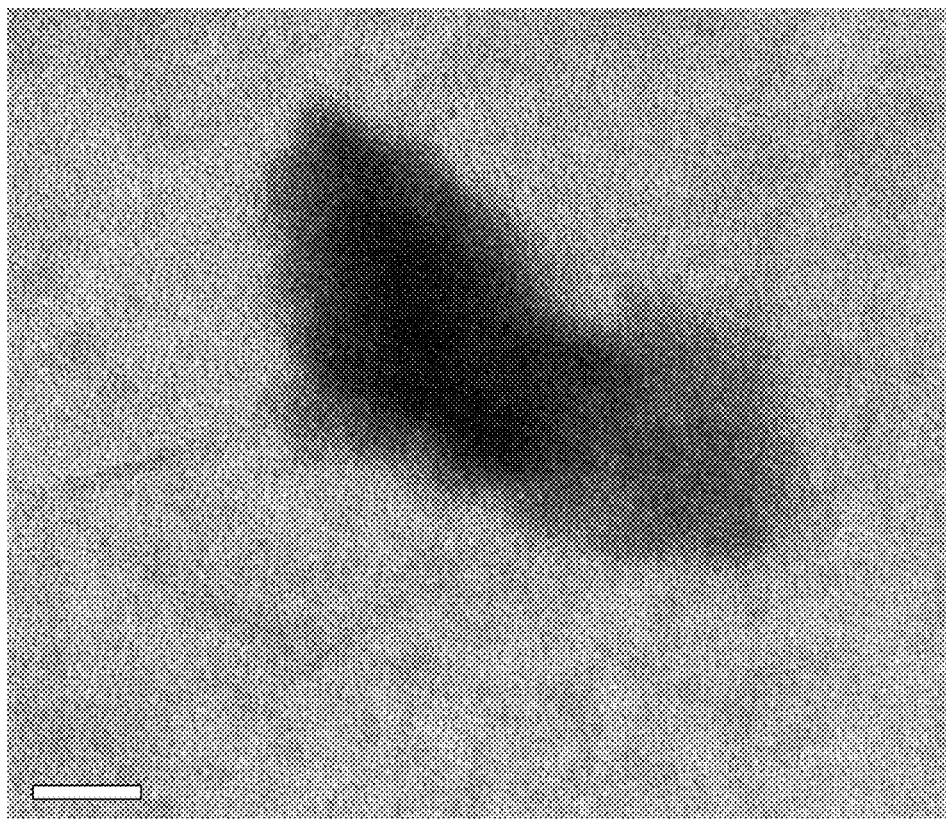
FIG. 8 is a TEM image of a functionalized superparamagnetic nanoparticle in accordance with FIG. 7; scale (left corner) is 20 nm.

The TEM image shown in FIG. 8 shows a dense coating of PEG polymer on a FeCo nanoparticle that was magnetically responsive. The diameter of the imaged nanoparticle-polymer structure is approximately 85 nm.

A number of implementations have been described. Nevertheless, it will be understood that various modifications may be made without departing from the spirit and scope of this disclosure.

The embodiments described herein are not intended to be exhaustive limited to the precise forms disclosed. Rather, the embodiments are chosen and described so that others skilled in the art can appreciate and understand the principles and practices described herein. This application is intended to cover adaptations or variations of the present subject matter.

All publications and patents mentioned herein are hereby incorporated by reference to the same extent as if each individual publication or patent was specifically and individually indicated. The publications and patents disclosed herein are provided solely for their disclosure. Nothing herein is to be construed as an admission that any publication and/or patent is prior art.

In the specification and in the claims, the terms "including" and "comprising" are open-ended terms and should be interpreted to mean "including, but not limited to . . . ." These terms are broader than, and therefore encompass, the more restrictive terms "consistently essentially of" and "consisting of."

As used herein and in the appended claims, the singular forms "a," "an," and "the" include plural reference unless the context clearly dictates otherwise. As such, the terms "a" (or "an"), "one or more" and "at least one" can be used interchangeably herein.

What is claimed is:

1. A method of preparing polymer-functionalized particles, the method comprising:
    (a) introducing a sputtering gas into a particle source under ultra-high vacuum conditions;
    (b) ionizing the gas;
    (c) passing the ionized gas through a plasma region in the opening(s) between targets or through the targets to liberate atoms from the target, thereby yielding a gas comprising the liberated atoms;
    (d) condensing the gas comprising the liberated atoms to yield particles;
    (e) collecting the particles on a collection device that comprises a substrate and a polymeric functionalization coating disposed on the substrate, wherein the particles impinge upon, and form bonds with molecules of the functionalization coating; and
    (f) washing collected polymer-functionalized particles obtained in step (e), thereby removing the functionalized particles coated with polymer molecules of the polymeric functionalization coating from the substrate.

2. The method according to claim 1 further comprising drying the collected polymer-functionalized particles of step (e).

3. The method according to claim 1 further comprising heating the collection device during or immediately after step (e).

4. The method according to claim 1, wherein the particles comprise FeCo, FeCo—FeCoO, FeCo—MgO, Fe—MgO, FeCo—ZnO, Fe—ZnO, FeZn, FeCo—Au, FeCo—Ag, FeCo—SiO$_2$, FeCo—TiO$_2$, Fe—Ag, Co—Au, C, Fe—Au, Fe—TiO$_2$, Fe$_5$Si$_3$, Fe$_3$Si, Fe$_{16}$N$_2$, FeN, FeSi$_3$—Au, Fe$_5$Si$_3$—SiO$_2$, Fe$_5$Si$_3$—Au, Fe$_{16}$N$_2$—Fe(N), Fe$_{16}$C$_2$, Fe$_{16}$C$_2$—Au, Fe$_{16}$N$_2$—Au, Fe$_{16}$N$_2$—Ag, Fe$_{16}$N$_2$—Al$_2$O$_3$, Fe$_{16}$N$_2$—TiO$_2$, or Fe$_{16}$N$_2$—SiO$_2$.

5. The method according to claim 1, wherein the polymeric functionalization coating is selected from the group consisting of vinyl polymers, fatty acids, polyethers, polyesters, acrylic polymers, and aromatic polymers.

6. The method according to claim 1, wherein the polymeric functionalization coating comprises a first functional group selected from the group consisting of hydroxyl, carboxyl, thiol, phosphate, sulfate, sulfide, and aldehyde.

7. The method according to claim 6, wherein the polymeric functionalization coating further comprises a second functional group.

8. The method according to claim 7, wherein the second functional group is different from the first functional group.

9. The method according to claim 7, wherein the second functional group is independently selected from the group consisting of hydroxyl, carboxyl, thiol, phosphate, sulfate, sulfide, and aldehyde.

10. The method according to claim 7, further comprising a compound bound to the second functional group.

11. The method according to claim 10, wherein the compound is selected from the group consisting of small molecules, proteins, nucleic acids, targeting ligands, peptides, antibodies, antibody fragments, detectable moieties, bioactive agents, and imaging agents.

12. The method according to claim 1, wherein the particles comprise nanoparticles.

13. The method according to claim 1, wherein the particles comprise magnetic particles.

14. The method according to claim 1, wherein the substrate is flexible.

15. The method according to claim 1 wherein the substrate is rigid.

16. The method according to claim 1, wherein the particles each have a metal core and the polymer-functionalized coating comprises at least one polymer, wherein the polymer is bound directly to the surface of the metal core.

17. The method according to claim 16, wherein the particles comprise magnetic particles.

* * * * *